United States Patent
Yates et al.

(10) Patent No.: US 9,549,732 B2
(45) Date of Patent: Jan. 24, 2017

(54) MOTOR-DRIVEN SURGICAL CUTTING INSTRUMENT

(71) Applicant: Ethicon Endo-Surgery, Inc., Cincinnati, OH (US)

(72) Inventors: David C. Yates, West Chester, OH (US); Frederick E. Shelton, IV, Hillsboro, OH (US); Bret W. Smith, Kings Mills, OH (US); Brett E. Swensgard, West Chester, OH (US); Ryan J. Laurent, Liberty Township, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 13/784,957

(22) Filed: Mar. 5, 2013

(65) Prior Publication Data
US 2013/0175322 A1 Jul. 11, 2013

Related U.S. Application Data

(63) Continuation of application No. 13/486,175, filed on Jun. 1, 2012, now Pat. No. 8,602,287, which is a
(Continued)

(51) Int. Cl.
*A61B 17/068* (2006.01)
*A61B 17/072* (2006.01)
(Continued)

(52) U.S. Cl.
CPC ....... *A61B 17/068* (2013.01); *A61B 17/07207* (2013.01); *A61B 17/105* (2013.01);
(Continued)

(58) Field of Classification Search
CPC ............ A61B 17/07207; A61B 17/068; A61B 2017/00398; A61B 2017/00734; A61B 2017/2927; A61B 2017/320052; A61B 2017/2923
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2012200178 B2 7/2013
CA 2458946 A1 3/2003
(Continued)

OTHER PUBLICATIONS

European Search Report for 09252253.1, Mar. 21, 2011 (5 pages).
(Continued)

*Primary Examiner* — Andrew M Tecco

(57) ABSTRACT

In various embodiments, a surgical stapler is disclosed. The stapler comprises a handle, a shaft, and a surgical end effector extending from the shaft. The stapler further comprises a firing member configured to move through a plurality of positions during a firing stroke, an electric motor configured to drive the firing member during the firing stroke, and a control system for controlling the electric motor. The control system comprises a battery and a pulse frequency modulation circuit configured to control the frequency of pulses supplied from the battery to the electric motor, wherein the pulse frequency modulation circuit is configured to optimize the speed applied to the firing member.

17 Claims, 23 Drawing Sheets

Related U.S. Application Data continuation of application No. 12/235,782, filed on Sep. 23, 2008, now Pat. No. 8,210,411.

(51) Int. Cl.

| | | |
|---|---|---|
| *A61B 17/10* | (2006.01) | |
| *A61B 17/3205* | (2006.01) | |
| *A61B 17/00* | (2006.01) | |
| *A61B 17/29* | (2006.01) | |
| *A61B 17/32* | (2006.01) | |

(52) U.S. Cl.
CPC .......... *A61B 17/32* (2013.01); *A61B 17/3205* (2013.01); *A61B 2017/00017* (2013.01); *A61B 2017/00398* (2013.01); *A61B 2017/00734* (2013.01); *A61B 2017/2923* (2013.01); *A61B 2017/2927* (2013.01); *A61B 2017/320052* (2013.01)

(58) Field of Classification Search
USPC .......... 227/175.1, 176.1, 178.1, 19; 606/170
See application file for complete search history.

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,441,096 A | 5/1948 | Happe |
| 2,526,902 A | 10/1950 | Rublee |
| 2,674,149 A | 4/1954 | Benson |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,166,072 A | 1/1965 | Sullivan, Jr. |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,494,533 A | 2/1970 | Green et al. |
| 3,551,987 A | 1/1971 | Wilkinson |
| 3,572,159 A | 3/1971 | Tschanz |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,169,990 A | 10/1979 | Lerdman |
| 4,198,982 A | 4/1980 | Fortner et al. |
| 4,207,898 A | 6/1980 | Becht |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,393,728 A | 7/1983 | Larson et al. |
| 4,396,139 A | 8/1983 | Hall et al. |
| 4,402,445 A | 9/1983 | Green |
| 4,408,692 A | 10/1983 | Siegel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,189 A | 1/1986 | Mabuchi |
| 4,566,620 A | 1/1986 | Green et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |

(56) References Cited

U.S. PATENT DOCUMENTS

| | | |
|---|---|---|
| 4,676,245 A | 6/1987 | Fukuda |
| 4,693,248 A | 9/1987 | Failla |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,834,720 A | 5/1989 | Blinkhorn |
| 4,844,068 A | 7/1989 | Arata et al. |
| 4,848,637 A | 7/1989 | Pruitt |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,192,288 A | 3/1993 | Thompson et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,285,945 A | 2/1994 | Brinkerhoff et al. |
| 5,289,963 A | 3/1994 | McGarry et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |

(56) References Cited

U.S. PATENT DOCUMENTS

| | | |
|---|---|---|
| 5,348,259 A | 9/1994 | Blanco et al. |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,368,015 A | 11/1994 | Wilk |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |

(56) References Cited

U.S. PATENT DOCUMENTS

| | | |
|---|---|---|
| 5,560,530 A | 10/1996 | Bolanos et al. |
| 5,560,532 A | 10/1996 | DeFonzo et al. |
| 5,562,239 A * | 10/1996 | Boiarski et al. ........... 227/175.2 |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |

(56) References Cited

U.S. PATENT DOCUMENTS

| | | |
|---|---|---|
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,096 A | 12/1998 | Igaki et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,971,916 A | 10/1999 | Koren |
| 5,988,479 A | 11/1999 | Palmer |
| 5,997,528 A | 12/1999 | Bisch et al. |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,050,472 A | 4/2000 | Shibata |
| 6,050,990 A | 4/2000 | Tankovich et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,063,097 A | 5/2000 | Oi et al. |
| 6,063,098 A | 5/2000 | Houser et al. |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |

(56) References Cited

U.S. PATENT DOCUMENTS

| | | |
|---|---|---|
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,338,737 B1 | 1/2002 | Toledano |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,454,781 B1 | 9/2002 | Witt et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |

(56) References Cited

U.S. PATENT DOCUMENTS

| | | |
|---|---|---|
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,843,403 B2 | 1/2005 | Whitman |
| 6,843,789 B2 | 1/2005 | Goble |
| 6,846,307 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,932,218 B2 | 8/2005 | Kosann et al. |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,868 B2 | 5/2006 | Greene et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |

(56) References Cited

U.S. PATENT DOCUMENTS

| | | |
|---|---|---|
| 7,066,879 B2 | 6/2006 | Fowler et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 * | 2/2007 | Kitagawa ............... 318/599 |
| 7,188,758 B2 | 3/2007 | Viola et al. |
| 7,189,207 B2 | 3/2007 | Viola |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,308,998 B2 | 12/2007 | Mastri et al. |
| 7,322,975 B2 | 1/2008 | Goble et al. |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,334,718 B2 | 2/2008 | McAlister et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,386,730 B2 | 6/2008 | Uchikubo |
| 7,388,217 B2 | 6/2008 | Buschbeck et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,076 B2 | 8/2008 | Racenet et al. |
| 7,407,078 B2 | 8/2008 | Shelton, IV et al. |
| 7,410,086 B2 | 8/2008 | Ortiz et al. |
| 7,416,101 B2 * | 8/2008 | Shelton et al. ............ 227/175.1 |
| 7,418,078 B2 | 8/2008 | Blanz et al. |
| RE40,514 E | 9/2008 | Mastri et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |

(56) References Cited

U.S. PATENT DOCUMENTS

| | | |
|---|---|---|
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,517,356 B2 | 4/2009 | Heinrich |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,563,862 B2 | 7/2009 | Sieg et al. |
| 7,566,300 B2 | 7/2009 | Devierre et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,003 B2 | 11/2009 | Stefanchik et al. |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,641,095 B2 | 1/2010 | Viola |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,204 B2 | 4/2010 | Viola |
| 7,699,844 B2 | 4/2010 | Utley et al. |
| 7,699,859 B2 | 4/2010 | Bombard et al. |
| 7,703,653 B2 | 4/2010 | Shah et al. |
| 7,708,180 B2 | 5/2010 | Murray et al. |
| 7,708,758 B2 | 5/2010 | Lee et al. |
| 7,714,239 B2 | 5/2010 | Smith |
| 7,717,312 B2 | 5/2010 | Beetel |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 * | 6/2010 | Whitman et al. .......... 227/180.1 |
| 7,744,627 B2 | 6/2010 | Orban, III et al. |
| 7,748,587 B2 | 7/2010 | Haramiishi et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,821 B2 | 8/2010 | Brunnen et al. |
| 7,766,894 B2 | 8/2010 | Weitzner et al. |
| 7,770,774 B2 | 8/2010 | Mastri et al. |
| 7,770,775 B2 | 8/2010 | Shelton, IV et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,401 B2 | 11/2010 | Manzo et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |

(56) References Cited

U.S. PATENT DOCUMENTS

| | | |
|---|---|---|
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,536 B2 | 12/2010 | Viola et al. |
| 7,845,537 B2 * | 12/2010 | Shelton et al. ............ 227/180.1 |
| 7,846,149 B2 | 12/2010 | Jankowski |
| 7,850,642 B2 | 12/2010 | Moll et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,871,418 B2 | 1/2011 | Thompson et al. |
| 7,887,530 B2 | 2/2011 | Zemlok et al. |
| 7,891,531 B1 | 2/2011 | Ward |
| 7,891,532 B2 | 2/2011 | Mastri et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,963,963 B2 | 6/2011 | Francischelli et al. |
| 7,966,799 B2 | 6/2011 | Morgan et al. |
| 7,967,180 B2 | 6/2011 | Scirica |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,056,788 B2 | 11/2011 | Mastri et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,091,756 B2 | 1/2012 | Viola |
| 8,097,017 B2 | 1/2012 | Viola |
| 8,100,310 B2 | 1/2012 | Zemlok |
| 8,108,072 B2 | 1/2012 | Zhao et al. |
| 8,113,410 B2 | 2/2012 | Hall et al. |
| 8,123,103 B2 | 2/2012 | Milliman |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,172,122 B2 | 5/2012 | Kasvikis et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,781 B2 | 6/2012 | Baxter, III et al. |
| 8,210,411 B2 * | 7/2012 | Yates et al. ................ 227/175.1 |
| 8,210,414 B2 | 7/2012 | Bettuchi et al. |
| 8,210,415 B2 | 7/2012 | Ward |
| 8,211,125 B2 | 7/2012 | Spivey |
| 8,215,531 B2 | 7/2012 | Shelton, IV et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,231,040 B2 | 7/2012 | Zemlok et al. |
| 8,231,041 B2 | 7/2012 | Marczyk et al. |
| 8,231,043 B2 | 7/2012 | Tarinelli et al. |
| 8,241,271 B2 | 8/2012 | Millman et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,292,155 B2 | 10/2012 | Shelton, IV et al. |
| 8,298,677 B2 | 10/2012 | Wiesner et al. |
| 8,308,040 B2 | 11/2012 | Huang et al. |
| 8,308,042 B2 | 11/2012 | Aranyi |
| 8,308,046 B2 | 11/2012 | Prommersberger |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,328,062 B2 | 12/2012 | Viola |
| 8,328,064 B2 | 12/2012 | Racenet et al. |
| 8,328,802 B2 | 12/2012 | Deville et al. |
| 8,333,313 B2 | 12/2012 | Boudreaux et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |

(56) References Cited

U.S. PATENT DOCUMENTS

| | | |
|---|---|---|
| 8,360,297 B2 | 1/2013 | Shelton, IV et al. |
| 8,365,973 B1 | 2/2013 | White et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,372,094 B2 | 2/2013 | Bettuchi et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,403,198 B2 | 3/2013 | Sorrentino et al. |
| 8,408,439 B2 | 4/2013 | Huang et al. |
| 8,409,079 B2 | 4/2013 | Okamoto et al. |
| 8,414,577 B2 | 4/2013 | Boudreaux et al. |
| 8,424,740 B2 | 4/2013 | Shelton, IV et al. |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,925 B2 | 6/2013 | Hull et al. |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,499,993 B2 | 8/2013 | Shelton, IV et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 2001/0025183 A1 | 9/2001 | Shahidi |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0117534 A1 | 8/2002 | Green et al. |
| 2002/0134811 A1* | 9/2002 | Napier et al. ............... 227/131 |
| 2002/0165541 A1 | 11/2002 | Whitman |
| 2003/0023316 A1 | 1/2003 | Brown et al. |
| 2003/0073981 A1* | 4/2003 | Whitman et al. ............... 606/1 |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0070369 A1 | 4/2004 | Sakahibara |
| 2004/0078037 A1 | 4/2004 | Batchelor et al. |
| 2004/0093024 A1 | 5/2004 | Lousararian et al. |
| 2004/0094597 A1* | 5/2004 | Whitman et al. ............... 227/180.1 |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |

(56) References Cited

U.S. PATENT DOCUMENTS

| | | |
|---|---|---|
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1* | 12/2006 | Viola et al. ................ 227/176.1 |
| 2006/0278681 A1 | 12/2006 | Viola et al. |
| 2006/0284730 A1 | 12/2006 | Schmid et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0048121 A1* | 3/2007 | Fristedt ........................ 415/13 |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0114261 A1 | 5/2007 | Ortiz et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1* | 8/2007 | Shelton et al. ............ 227/178.1 |
| 2007/0175956 A1* | 8/2007 | Swayze et al. ............ 227/178.1 |
| 2007/0175958 A1* | 8/2007 | Shelton et al. ............ 227/178.1 |
| 2007/0175959 A1* | 8/2007 | Shelton et al. ............ 227/178.1 |
| 2007/0175964 A1* | 8/2007 | Shelton et al. ............ 227/180.1 |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0286892 A1 | 12/2007 | Herzberg et al. |
| 2007/0288044 A1 | 12/2007 | Jinno et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0167522 A1 | 7/2008 | Giordano et al. |
| 2008/0169328 A1 | 7/2008 | Shelton |
| 2008/0169329 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0297287 A1 | 12/2008 | Shachar et al. |

(56) References Cited

U.S. PATENT DOCUMENTS

| | | |
|---|---|---|
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0048589 A1 | 2/2009 | Takashino et al. |
| 2009/0054908 A1 | 2/2009 | Zand et al. |
| 2009/0078736 A1 | 3/2009 | Van Lue |
| 2009/0088774 A1 | 4/2009 | Swarup et al. |
| 2009/0090763 A1* | 4/2009 | Zemlok et al. ............ 227/175.2 |
| 2009/0093728 A1 | 4/2009 | Hyde et al. |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0198272 A1 | 8/2009 | Kerver et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0001036 A1* | 1/2010 | Marczyk et al. .......... 227/175.1 |
| 2010/0012704 A1 | 1/2010 | Tarinelli Racenet et al. |
| 2010/0023024 A1 | 1/2010 | Zeiner et al. |
| 2010/0049084 A1 | 2/2010 | Nock et al. |
| 2010/0057087 A1 | 3/2010 | Cha |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0087840 A1 | 4/2010 | Ebersole et al. |
| 2010/0089970 A1 | 4/2010 | Smith et al. |
| 2010/0094289 A1 | 4/2010 | Taylor et al. |
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0179540 A1 | 7/2010 | Marczyk et al. |
| 2010/0186219 A1 | 7/2010 | Smith |
| 2010/0193566 A1 | 8/2010 | Schieb et al. |
| 2010/0200637 A1 | 8/2010 | Beetel |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0268030 A1 | 10/2010 | Viola et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0003528 A1 | 1/2011 | Lam |
| 2011/0006099 A1 | 1/2011 | Hall et al. |
| 2011/0006101 A1 | 1/2011 | Hall et al. |
| 2011/0011916 A1 | 1/2011 | Levine |
| 2011/0017801 A1 | 1/2011 | Zemlok et al. |
| 2011/0022032 A1* | 1/2011 | Zemlok et al. .................. 606/1 |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0036890 A1 | 2/2011 | Ma |
| 2011/0060363 A1 | 3/2011 | Hess et al. |
| 2011/0068148 A1 | 3/2011 | Hall et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0114700 A1 | 5/2011 | Baxter, III et al. |
| 2011/0118754 A1 | 5/2011 | Dachs, II et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0163147 A1 | 7/2011 | Laurent et al. |
| 2011/0174861 A1 | 7/2011 | Shelton, IV et al. |
| 2011/0174862 A1 | 7/2011 | Shelton, IV et al. |
| 2011/0178536 A1 | 7/2011 | Kostrzewski |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0022523 A1 | 1/2012 | Smith et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |

(56) References Cited

U.S. PATENT DOCUMENTS

| | | |
|---|---|---|
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138658 A1 | 6/2012 | Ullrich et al. |
| 2012/0138660 A1 | 6/2012 | Shelton, IV |
| 2012/0150192 A1 | 6/2012 | Dachs, II et al. |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0203247 A1 | 8/2012 | Shelton, IV et al. |
| 2012/0209289 A1 | 8/2012 | Duque et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur |
| 2012/0241497 A1 | 9/2012 | Mandakolathur |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0283707 A1 | 11/2012 | Giordano et al. |
| 2012/0283748 A1 | 11/2012 | Ortiz et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012931 A1 | 1/2013 | Spivey et al. |
| 2013/0012957 A1 | 1/2013 | Shelton, IV et al. |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0103024 A1 | 4/2013 | Monson et al. |
| 2013/0105551 A1 | 5/2013 | Zingman |
| 2013/0116668 A1 | 5/2013 | Shelton, IV et al. |
| 2013/0116669 A1 | 5/2013 | Shelton, IV et al. |
| 2013/0123822 A1 | 5/2013 | Wellman et al. |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175321 A1 | 7/2013 | Shelton, IV et al. |
| 2013/0181030 A1 | 7/2013 | Hess et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |

(56) References Cited

U.S. PATENT DOCUMENTS

| | | |
|---|---|---|
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |

FOREIGN PATENT DOCUMENTS

| | | |
|---|---|---|
| CA | 2512960 A1 | 1/2006 |
| CA | 2514274 A1 | 1/2006 |
| CN | 2488482 Y | 5/2002 |
| CN | 1523725 A | 8/2004 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |

(56) References Cited

FOREIGN PATENT DOCUMENTS

| | | |
|---|---|---|
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A1 | 8/2007 |
| EP | 1813207 A1 | 8/2007 |
| EP | 1813209 A1 | 8/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 2039302 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 B1 | 6/2009 |
| EP | 1550413 B1 | 6/2009 |
| EP | 1719461 B1 | 6/2009 |
| EP | 1745748 B1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1875870 B1 | 12/2009 |
| EP | 2151204 A1 | 2/2010 |
| EP | 2165660 A2 | 3/2010 |

(56) References Cited

FOREIGN PATENT DOCUMENTS

| | | |
|---|---|---|
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 2198787 A1 | 6/2010 |
| EP | 1647286 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 1994890 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 2153781 B1 | 11/2011 |
| EP | 1847225 B1 | 12/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| EP | 2090252 B1 | 10/2012 |
| EP | 2517637 A1 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 05-084252 A | 4/1993 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | 7051273 A | 2/1995 |
| JP | 7-124166 A | 5/1995 |
| JP | 07-171163 | 7/1995 |
| JP | 7-255735 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 09-501081 A | 2/1997 |
| JP | H 09-501577 A | 2/1997 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-164066 | 6/2003 |
| JP | 2003-521301 A | 7/2003 |
| JP | 2004-162035 A | 6/2004 |
| JP | 2004-229976 A | 8/2004 |
| JP | 2004-531280 A | 10/2004 |
| JP | 2004-532084 A | 10/2004 |
| JP | 2004-329624 A | 11/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2005-335432 A | 12/2005 |
| JP | 2006-034975 A | 2/2006 |
| JP | 2006-34977 A | 2/2006 |
| JP | 2006-034980 A | 2/2006 |
| JP | 2006-506106 A | 2/2006 |
| JP | 2006-187649 A | 7/2006 |
| JP | 2006-218297 A | 8/2006 |
| JP | 2006-281405 A | 10/2006 |
| JP | 2006-346445 A | 12/2006 |
| JP | 2007-61628 A | 3/2007 |
| JP | 2007-098130 A | 4/2007 |
| JP | 3906843 B2 | 4/2007 |
| JP | 2007-117725 A | 5/2007 |
| JP | 2007-222615 A | 6/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 2007-325922 A | 12/2007 |
| JP | 2008-68073 A | 3/2008 |
| JP | 2008-283459 A | 11/2008 |
| JP | 2009-506799 A | 2/2009 |
| JP | 2009-106752 A | 5/2009 |
| JP | 2009-539420 A | 11/2009 |
| JP | 2010-098844 A | 4/2010 |
| RU | 1814161 A1 | 5/1993 |
| RU | 2008830 C1 | 3/1994 |
| RU | 2141279 C1 | 11/1999 |
| RU | 2187249 C2 | 8/2002 |
| RU | 2189091 C2 | 9/2002 |
| RU | 2225170 C2 | 3/2004 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |

(56) References Cited

FOREIGN PATENT DOCUMENTS

| | | |
|---|---|---|
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |

(56) References Cited

FOREIGN PATENT DOCUMENTS

| | | |
|---|---|---|
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/046394 A1 | 4/2009 |
| WO | WO 2009/137761 A2 | 11/2009 |
| WO | WO 2009/143092 A1 | 11/2009 |
| WO | WO 2010/028332 A2 | 3/2010 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044820 A1 | 4/2012 |
| WO | WO 2012/044844 A2 | 4/2012 |

OTHER PUBLICATIONS

U.S. Appl. No. 12/031,556, filed Feb. 14, 2008.
U.S. Appl. No. 12/031,573, filed Feb. 14, 2008.
U.S. Appl. No. 12/032,024, filed Feb. 15, 2008.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property—Durometer Hardness," (Published Aug. 2000).
ASTM procedure D2240-05, "Standard Test Method for Rubber Property—Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Stapler™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.

(56) References Cited

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
U.S. Appl. No. 12/031,542, filed Feb. 14, 2008.
U.S. Appl. No. 13/369,629, filed Feb. 9, 2012.
U.S. Appl. No. 13/958,922, filed Aug. 5, 2013.
U.S. Appl. No. 13/958,932, filed Aug. 5, 2013.
U.S. Appl. No. 13/965,877, filed Aug. 13, 2013.
U.S. Appl. No. 13/967,388, filed Aug. 15, 2013.
U.S. Appl. No. 13/967,449, filed Aug. 15, 2013.
U.S. Appl. No. 13/967,716, filed Aug. 15, 2013.
U.S. Appl. No. 13/970,971, filed Aug. 20, 2013.
U.S. Appl. No. 13/971,006, filed Aug. 20, 2013.
U.S. Appl. No. 13/971,012, filed Aug. 20, 2013.
U.S. Appl. No. 13/971,022, filed Aug. 20, 2013.
U.S. Appl. No. 13/536,271, filed Jun. 28, 2012.
U.S. Appl. No. 13/536,288, filed Jun. 28, 2012.
U.S. Appl. No. 13/536,277, filed Jun. 28, 2012.
U.S. Appl. No. 13/536,295, filed Jun. 28, 2012.
U.S. Appl. No. 13/536,326, filed Jun. 28, 2012.
U.S. Appl. No. 13/536,303, filed Jun. 28, 2012.
U.S. Appl. No. 13/536,393, filed Jun. 28, 2012.
U.S. Appl. No. 13/536,362, filed Jun. 28, 2012.
U.S. Appl. No. 13/536,284, filed Jun. 28, 2012.
U.S. Appl. No. 13/536,374, filed Jun. 28, 2012.
U.S. Appl. No. 13/536,292, filed Jun. 28, 2012.
U.S. Appl. No. 13/536,301, filed Jun. 28, 2012.
U.S. Appl. No. 13/536,313, filed Jun. 28, 2012.
U.S. Appl. No. 13/536,323, filed Jun. 28, 2012.
U.S. Appl. No. 13/536,379, filed Jun. 28, 2012.
U.S. Appl. No. 13/536,386, filed Jun. 28, 2012.
U.S. Appl. No. 13/536,360, filed Jun. 28, 2012.
U.S. Appl. No. 13/536,335, filed Jun. 28, 2012.
U.S. Appl. No. 13/536,417, filed Jun. 28, 2012.
U.S. Appl. No. 13/763,035, filed Feb. 8, 2013.
U.S. Appl. No. 13/763,042, filed Feb. 8, 2013.
U.S. Appl. No. 13/763,048, filed Feb. 8, 2013.
U.S. Appl. No. 13/763,054, filed Feb. 8, 2013.
U.S. Appl. No. 13/763,065, filed Feb. 8, 2013.
U.S. Appl. No. 14/012,831, filed Aug. 28, 2013.
U.S. Appl. No. 14/013,755, filed Aug. 29, 2013.
U.S. Appl. No. 14/014,800, filed Aug. 30, 2013.
U.S. Appl. No. 14/015,200, filed Aug. 30, 2013.
U.S. Appl. No. 14/015,435, filed Aug. 30, 2013.
U.S. Appl. No. 14/015,509, filed Aug. 30, 2013.
U.S. Appl. No. 14/064,940, filed Oct. 28, 2013.

\* cited by examiner

MOTOR-DRIVEN SURGICAL CUTTING INSTRUMENT

CROSS REFERENCE TO RELATED APPLICATIONS

This application is a continuation application under 35 U.S.C. §120 of U.S. patent application Ser. No. 13/486,175, entitled MOTOR-DRIVEN SURGICAL CUTTING INSTRUMENT, filed on Jun. 1, 2012, now U.S. Pat. No. 8,602,287, which is a continuation application under 35 U.S.C. §120 of U.S. application Ser. No. 12/235,782, entitled MOTOR-DRIVEN SURGICAL CUTTING INSTRUMENT, filed Sep. 23, 2008, now U.S. Pat. No. 8,210,411, the disclosures of each is hereby incorporated by reference in their entirety.

BACKGROUND

Surgical staplers are used to simultaneously make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples—one on each side of the knife channel. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. Simultaneously, a cutting instrument (or knife) is drawn distally along the jaw member so that the clamped tissue is cut and fastened (e.g., stapled) at the same time.

An example of a surgical stapler suitable for endoscopic applications is described in published U.S. patent application Pub. No. 2004/0232196 A1, entitled, "Surgical stapling instrument having separate distinct closing and firing systems," the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling actions avoid complications that may arise when performing such actions sequentially with different surgical tools that respectively only sever or staple.

Motor-driven endocutters are known in the art. In such devices, a motor powers the cutting and fastening action of the instrument. It is also known to use an on-board battery, located in the handle of the instrument, to power the motor. Published U.S. patent application Pub. No. 2007/0175952 A1, entitled "Motor-driven surgical cutting and fastening instrument with loading force feedback," the disclosure of which is herein incorporated by reference in its entirety, describes one such motor-driven surgical instrument.

SUMMARY

In various embodiments, a surgical instrument for cutting and stapling tissue is provided. The surgical instrument comprises a handle comprising an electric motor and a control system for controlling the electric motor. The control system comprises, one, a battery operably coupleable to the electric motor, the battery configured to supply pulses to the electric motor and, two, a pulse width modulation circuit operably coupleable to the battery, the pulse width modulation circuit configured to control the duration of pulses supplied from the battery to the electric motor. The surgical instrument further comprises a shaft extending from the handle and an end effector extending from the shaft. The end effector comprises a replaceable staple cartridge comprising a plurality of staples for stapling tissue and a cutting element for cutting tissue, wherein the cutting element is configured to move at least partially through the end effector during a firing stroke to deploy the staples, wherein the electric motor is configured to drive the cutting element with an applied power during the firing stroke at a firing speed, wherein the pulse width modulation circuit is configured to reduce the speed of the cutting element to below the firing speed at various times during the firing stroke, and wherein the applied power applied to the cutting element is optimized by the pulse width modulation circuit. The end effector further comprises a proximal end, a cartridge lockout mechanism positioned in a lockout region of the end effector, wherein the pulse width modulation circuit is configured to modulate the speed of the cutting element below the firing speed as the cutting element travels within the lockout region, and a distal end, wherein the pulse width modulation circuit is configured to modulate the speed of the cutting element below the firing speed as the cutting element approaches the distal end.

In various embodiments, a surgical stapler is provided. The surgical stapler comprises a handle, a shaft extending from the handle, and a surgical end effector extending from the shaft, wherein the surgical end effector comprises a replaceable staple cartridge. The surgical stapler further comprises a firing member configured to move through a plurality of positions during a firing stroke, an electric motor configured to drive the firing member with a speed during the firing stroke, and a control system for controlling the electric motor. The control system comprises, one, a battery operably engageable with the electric motor, the battery configured to supply pulses to the electric motor, and, two, a pulse width modulation circuit operably engageable with the battery, the pulse width modulation circuit configured to control the duration of pulses supplied from the battery to the electric motor, wherein the pulse width modulation circuit is configured to optimize the speed applied to the firing member from the electric motor. The firing member is configured to move at least partially through the surgical end effector during the firing stroke at a firing speed, wherein the pulse width modulation circuit is configured to reduce the speed of the firing member to below the firing speed at various times during the firing stroke. The surgical end effector further comprises a proximal end, a cartridge lockout mechanism positioned in a lockout region, wherein the pulse width modulation circuit is configured to modulate the speed of the firing member below the firing speed as the firing member travels within the lockout region, and a distal end, wherein the pulse width modulation circuit is configured to modulate the speed of the firing member below the firing speed as the firing member approaches the distal end.

In various embodiments, a surgical stapler is provided. The surgical stapler comprises a handle, a shaft extending from the handle, and a surgical end effector extending from the shaft, wherein the surgical end effector comprises a replaceable staple cartridge. The surgical stapler further comprises a firing member configured to move through a plurality of positions during a firing stroke, an electric motor configured to drive the firing member during the firing stroke, and a control system for controlling the electric motor. the control system comprises, one, a battery operably engageable with the electric motor, the battery configured to supply pulses to the electric motor, and, two, a pulse frequency modulation circuit operably engageable with the battery, the pulse frequency modulation circuit configured to control the frequency of pulses supplied from the battery to the electric motor, wherein the pulse frequency modulation circuit is configured to optimize the speed applied to the firing member from the electric motor. The firing member is configured to move at least partially through the surgical end effector during the firing stroke at a firing speed, wherein the pulse frequency modulation circuit is configured to reduce the speed of the firing member to below the firing speed at various times during the firing stroke. T he surgical end effector further comprises a proximal end and a distal end, wherein the pulse frequency modulation circuit is configured to modulate the speed of the firing member below the firing speed as the firing member approaches the distal end.

These and other benefits of the present invention will be apparent from the description below.

FIGURES

Various embodiments of the present invention are described herein by way of example in conjunction with the following figures, wherein:

FIGS. 1, 2, and 24 depict a surgical instrument with an articulatable end effector according to various embodiments of the present invention;

Figure 12:
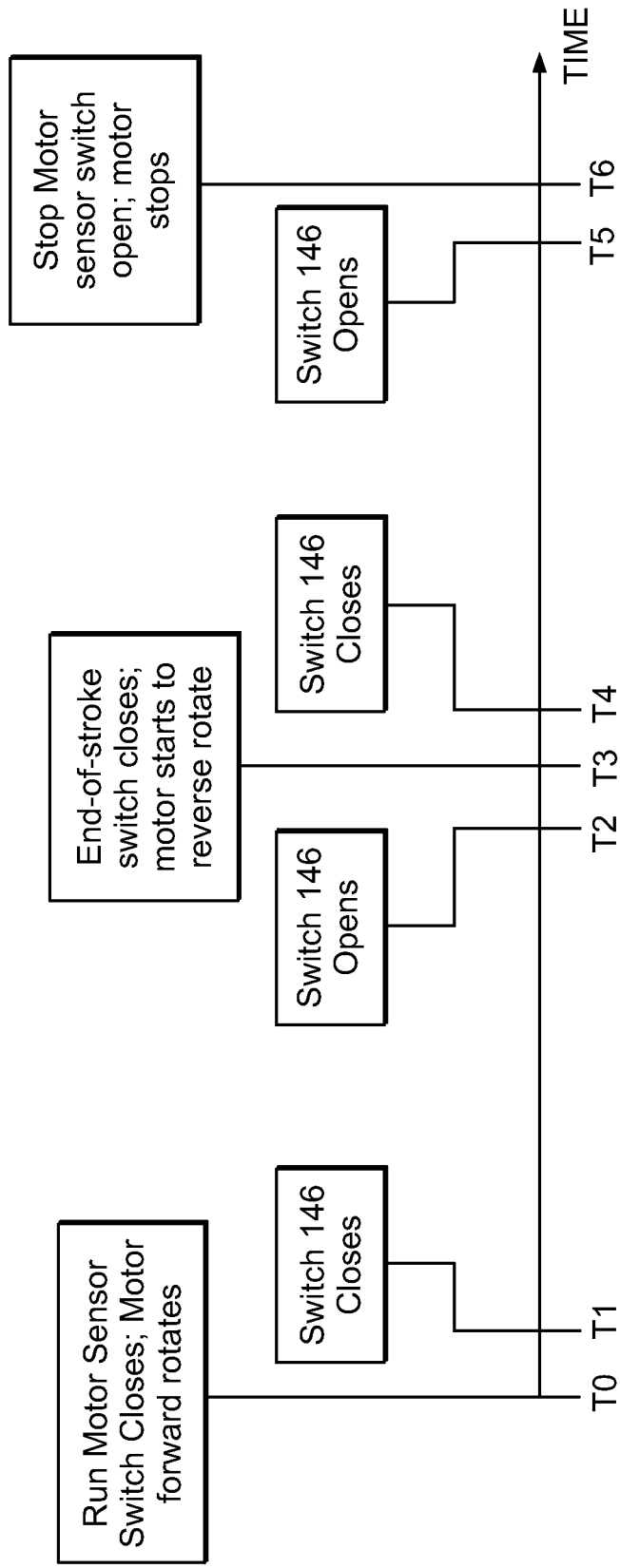
Figure 19:
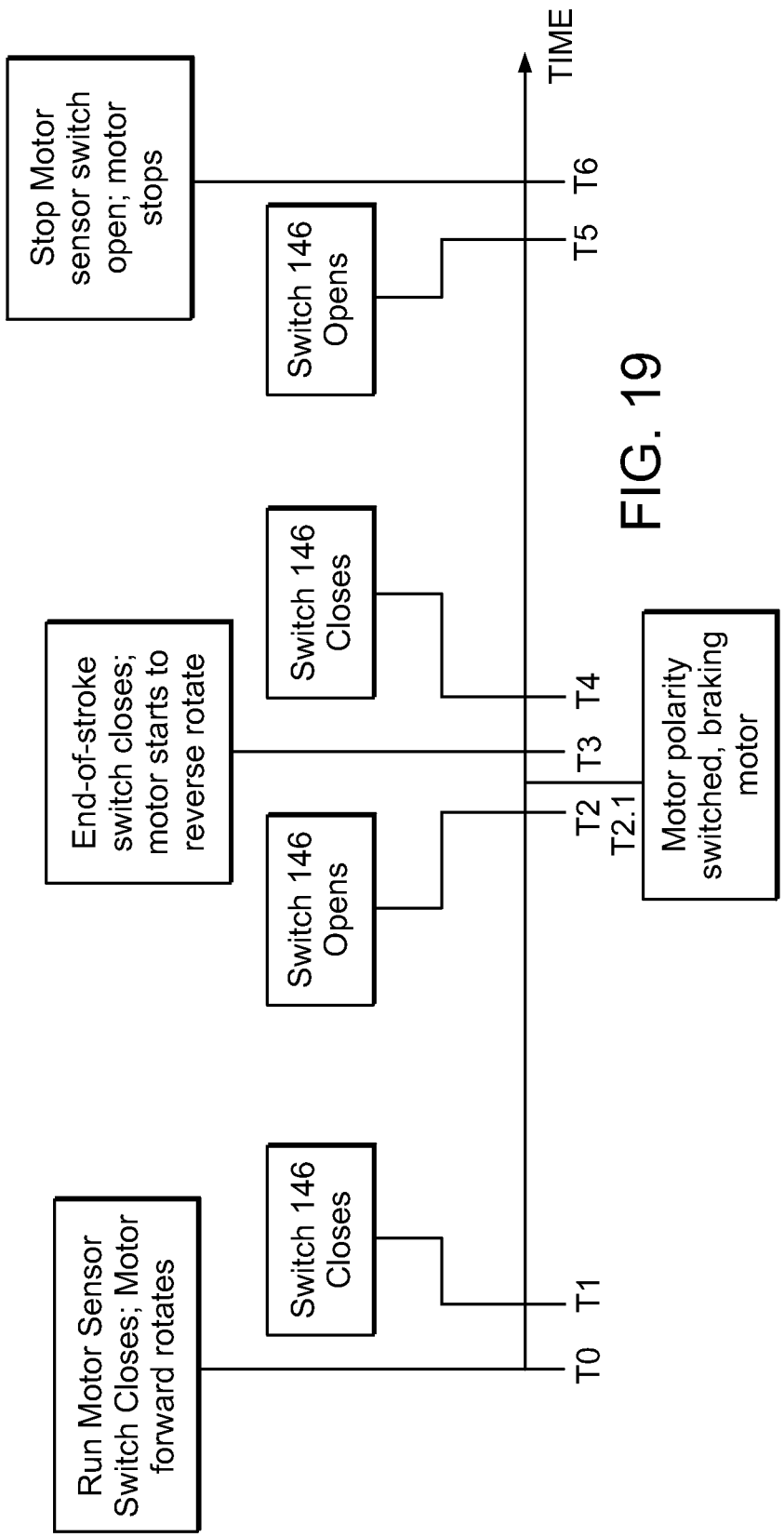
Figure 20:
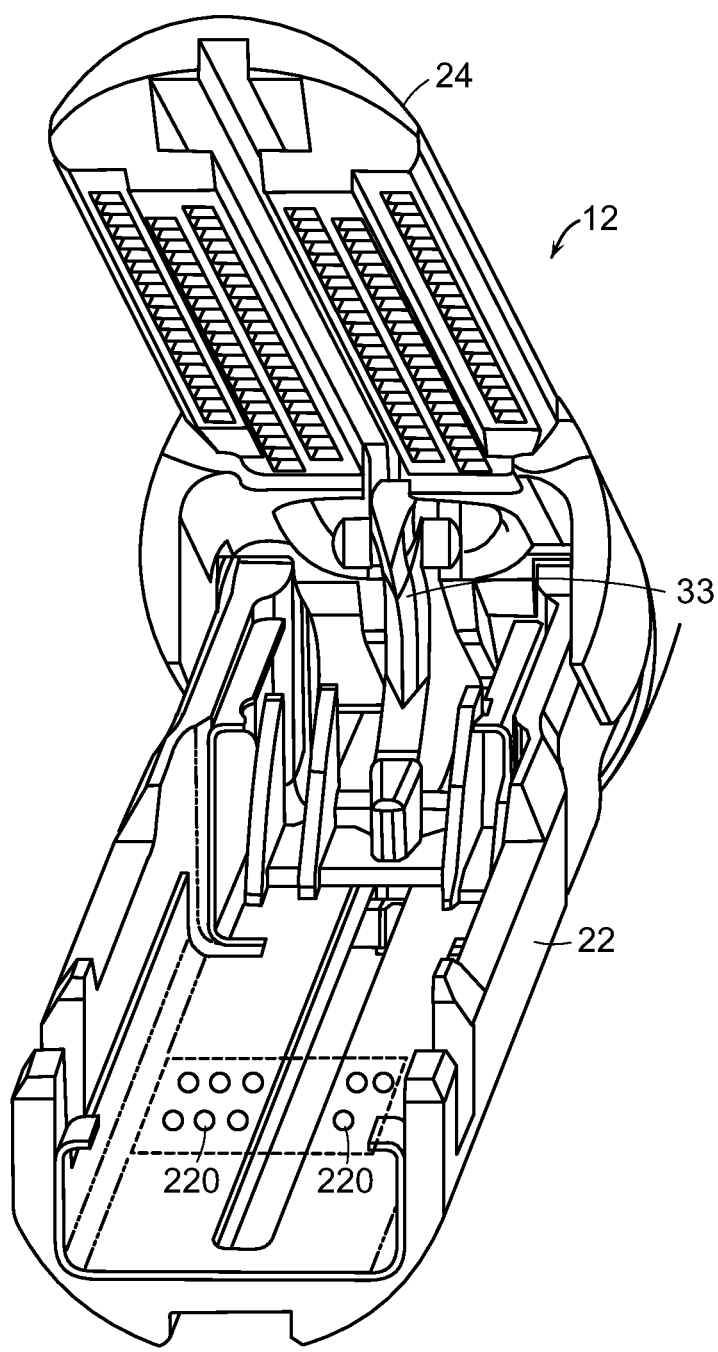
Figure 21:
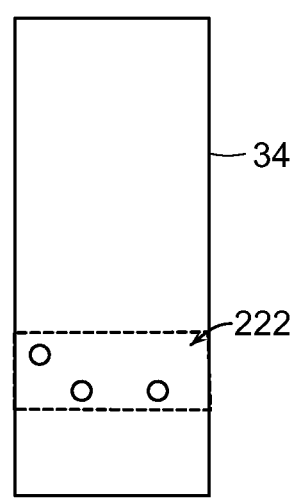
Figure 23:
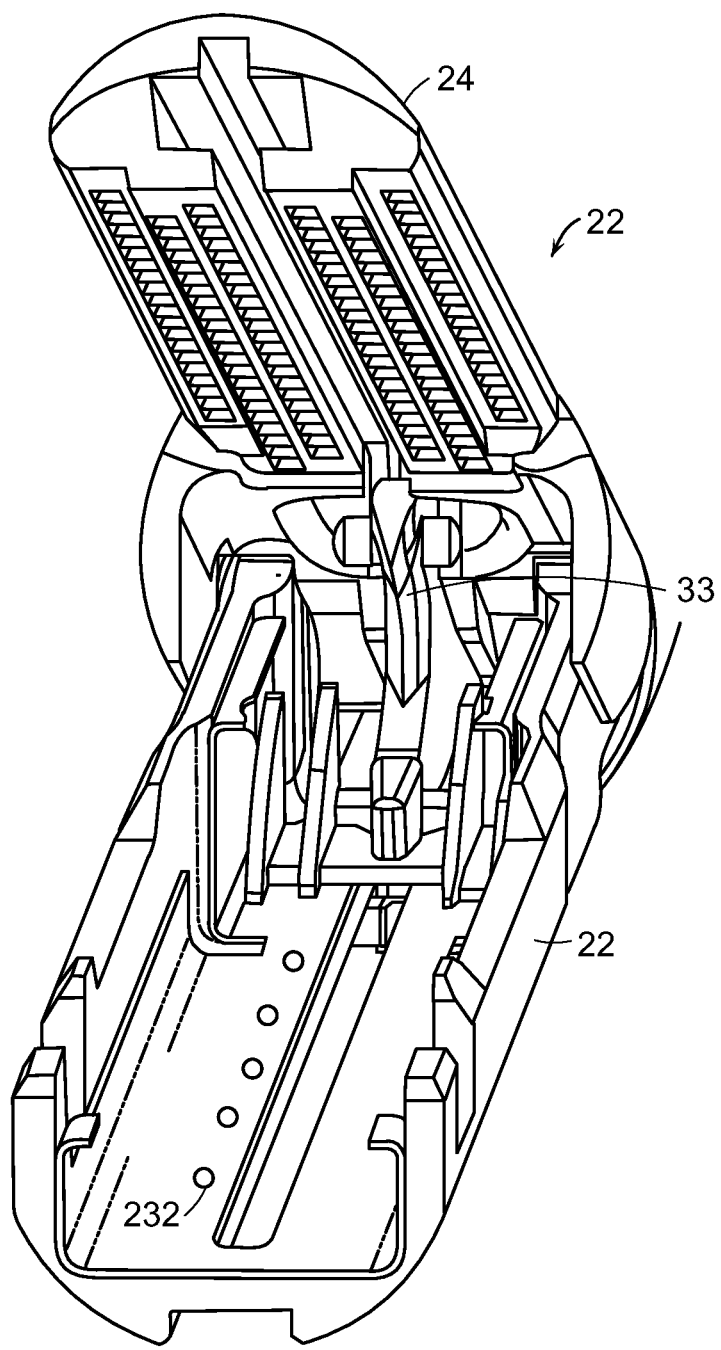
Figure 22:
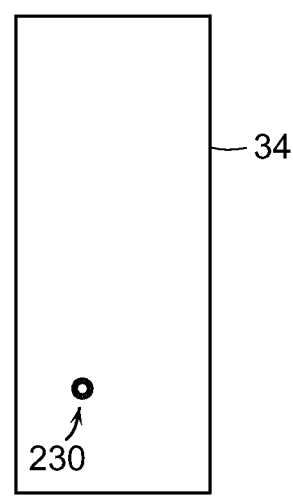

FIGS. 11, 13-18, and 25 are diagrams of motor control circuit according to various embodiments of the present invention;

FIGS. 12 and 19 are timing diagrams illustrating operation of the instrument according to various embodiments of the present invention;

FIGS. 20 and 23 are diagrams of the end effector, without a cartridge, according to various embodiments of the present invention; and FIGS. 21-22 are diagrams of a replaceable cartridge according to various embodiments of the present invention.

DESCRIPTION

Figure 1:
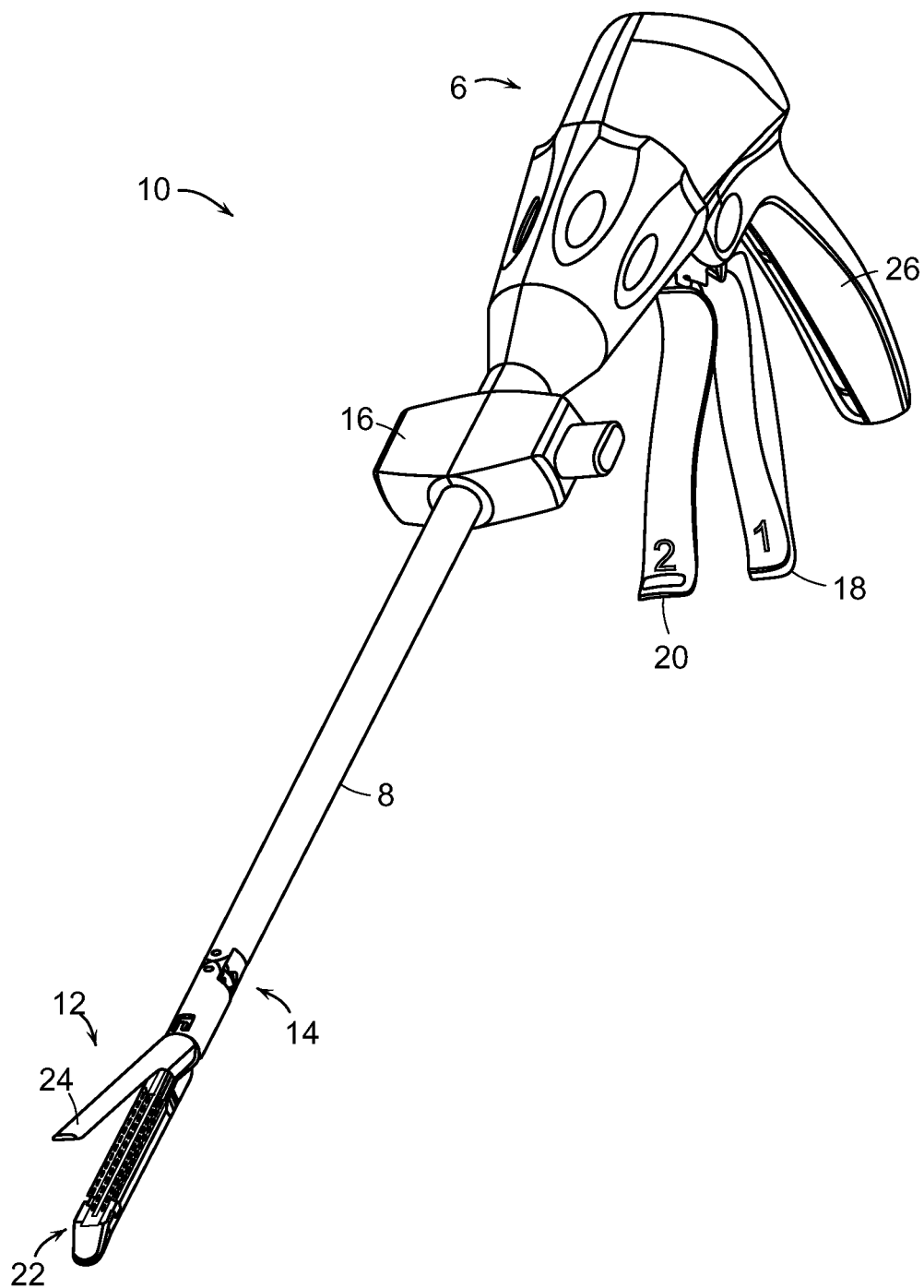
Figure 2:
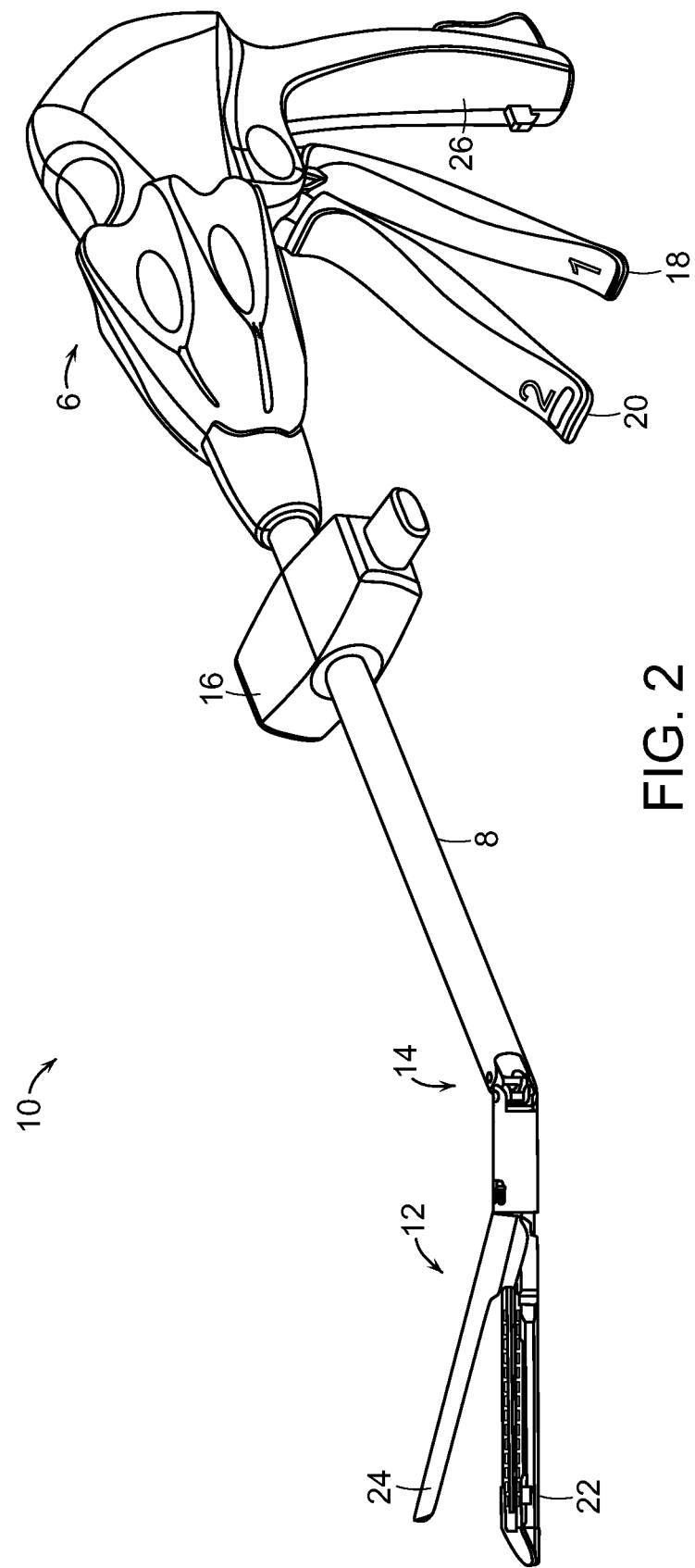

FIGS. 1 and 2 depict a motor-driven surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that the invention is not so limited and that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in U.S. Pat. No. 5,403,312 and commonly assigned U.S. patent application Ser. No. 12/031,573, entitled "Surgical cutting and fastening instrument having RF electrodes, filed Feb. 14, 2008, both of which are incorporated by reference in their entirety.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in published U.S. patent application Pub. No. 2007/0158385 A1, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures, when the anvil 24 is in its clamped position, effective stapling and severing of tissue clamped in the end effector 12. The handle 6 includes a downwardly extending pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

In operational use, the closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated.

The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as disclosed in published U.S. patent application Pub. No. 2007/0175955, entitled "Surgical cutting and fastening instrument with closure trigger locking mechanism," which is incorporated herein by reference in its entirety.

Figure 3:
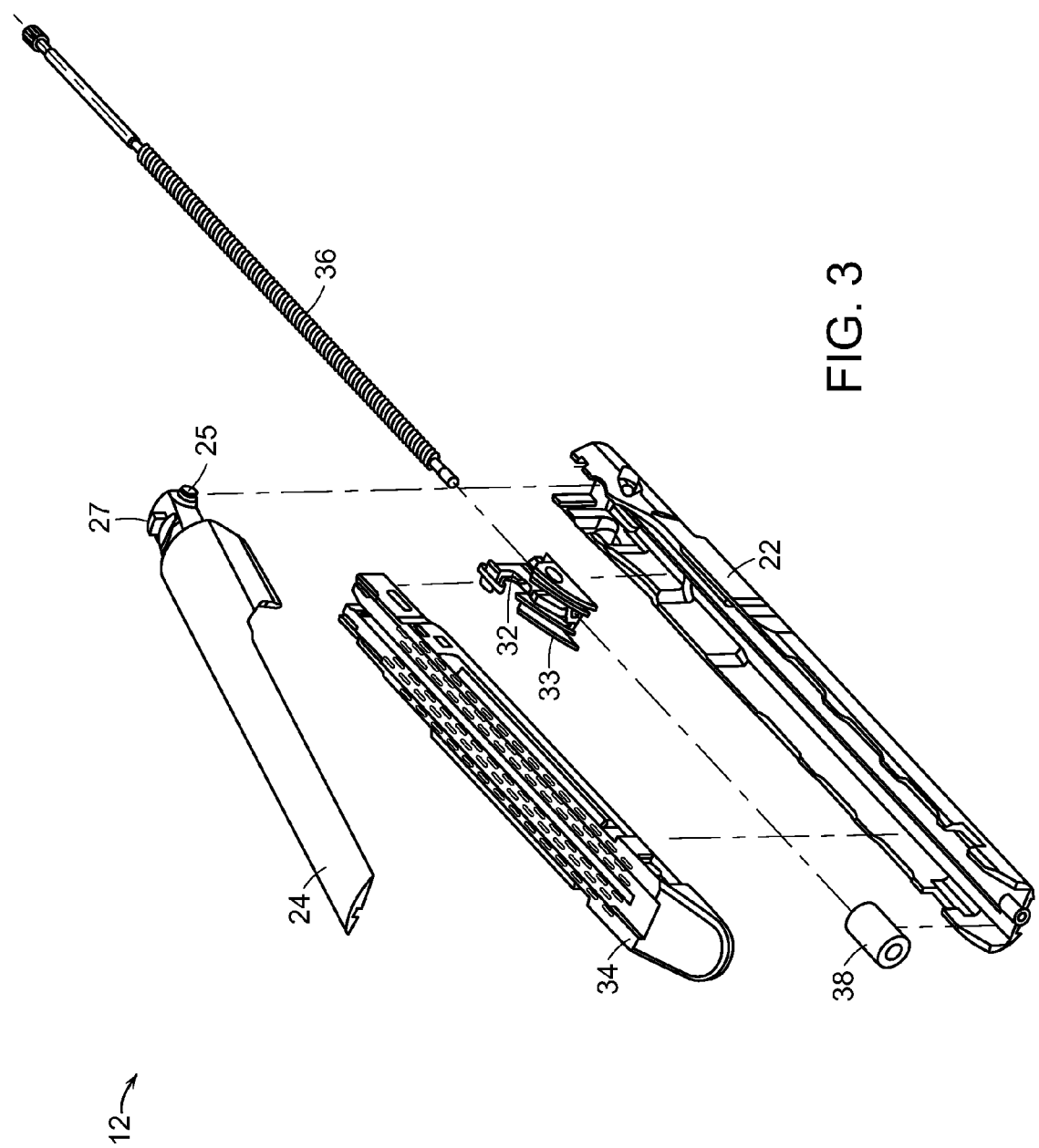
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22 between open and closed positions, respectively. The anvil 24 may also include a tab 27 at its proximate end that is inserted into a component of the mechanical closure system (described further below) to open and close the anvil 24. When the closure trigger 18 is actuated, that is, drawn in by a user of the instrument 10 toward the pistol grip portion 26, the anvil 24 may pivot about the pivot point 25 into the clamped or closed position. If clamping of the end effector 12 is satisfactory, the operator may actuate the firing trigger 20, which causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "Surgical stapling instrument incorporating an E-beam firing mechanism," which is incorporated herein by reference in its entirety, provides more details about such two-stroke cutting and fastening instruments. In various embodiments, the sled 33 may be part of the cartridge 34, such that when the knife 32 refracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTROSURGICAL HEMOSTATIC DEVICE WITH RECESSED AND/OR OFFSET ELECTRODES" to Yates et al., which are incorporated herein by reference in their entirety, disclose an endoscopic cutting instrument that uses RF energy to seal the severed tissue. Published U.S. patent application Pub. No. 2007/0102453 A1 to Jerome R. Morgan, et al. and published U.S. patent application Pub. No. 2007/0102452 A1 to Frederick E. Shelton, IV, et al., which are also incorporated herein by reference, disclose endoscopic cutting instruments that use adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
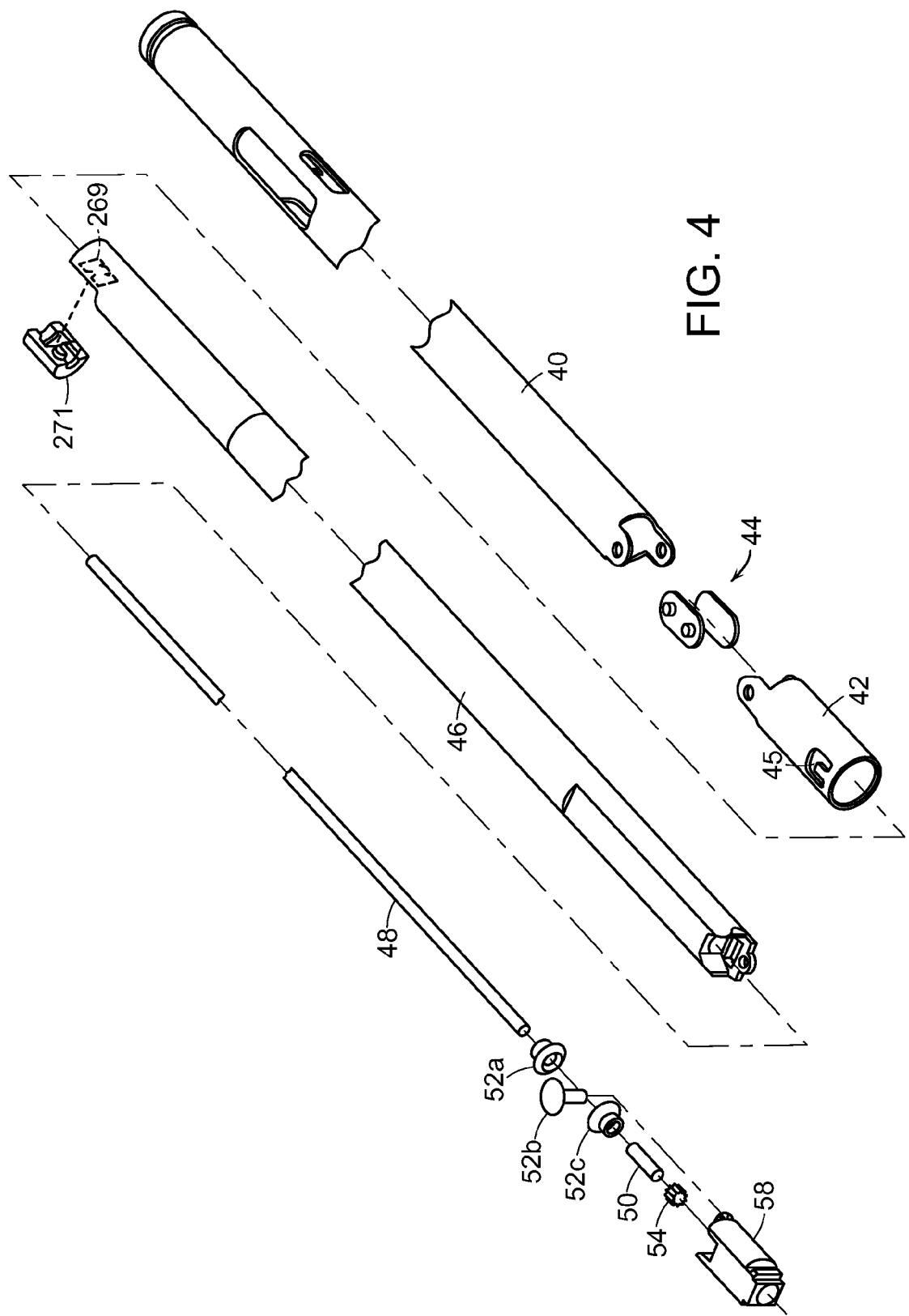
Figure 5:
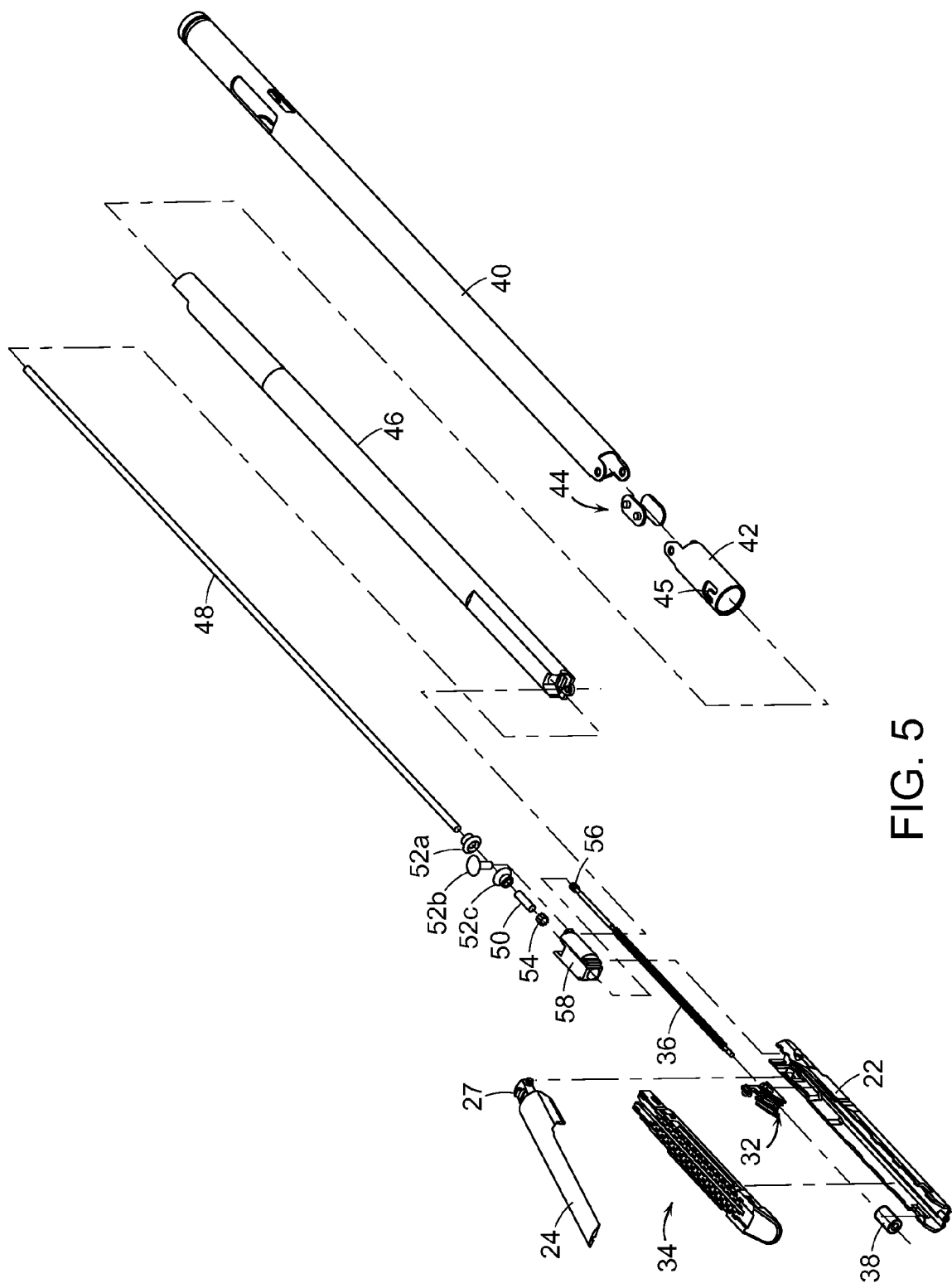
Figure 6:
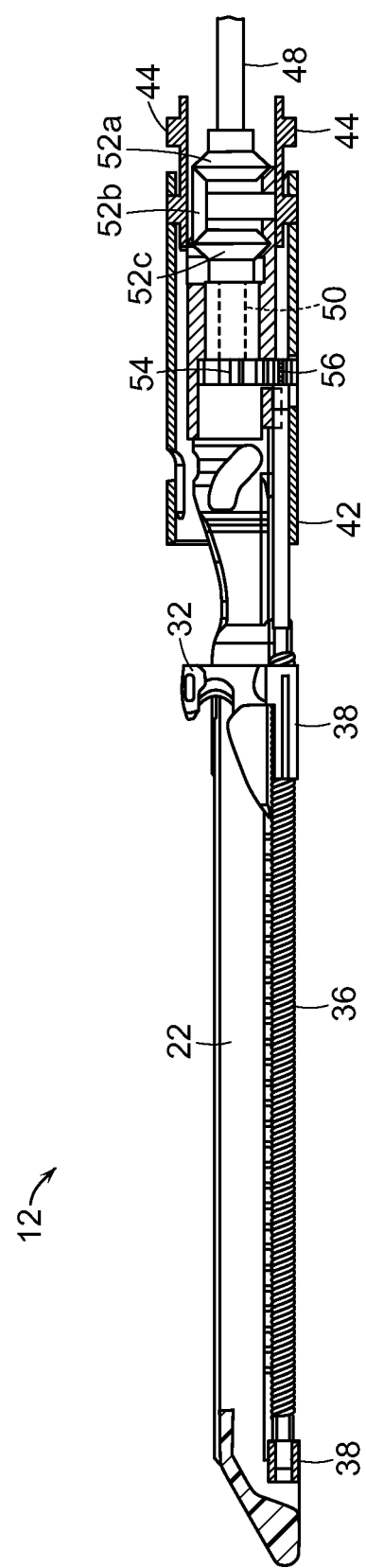
FIG. 6 is a side view of the end effector according to various embodiments of the present invention.
Figure 7:
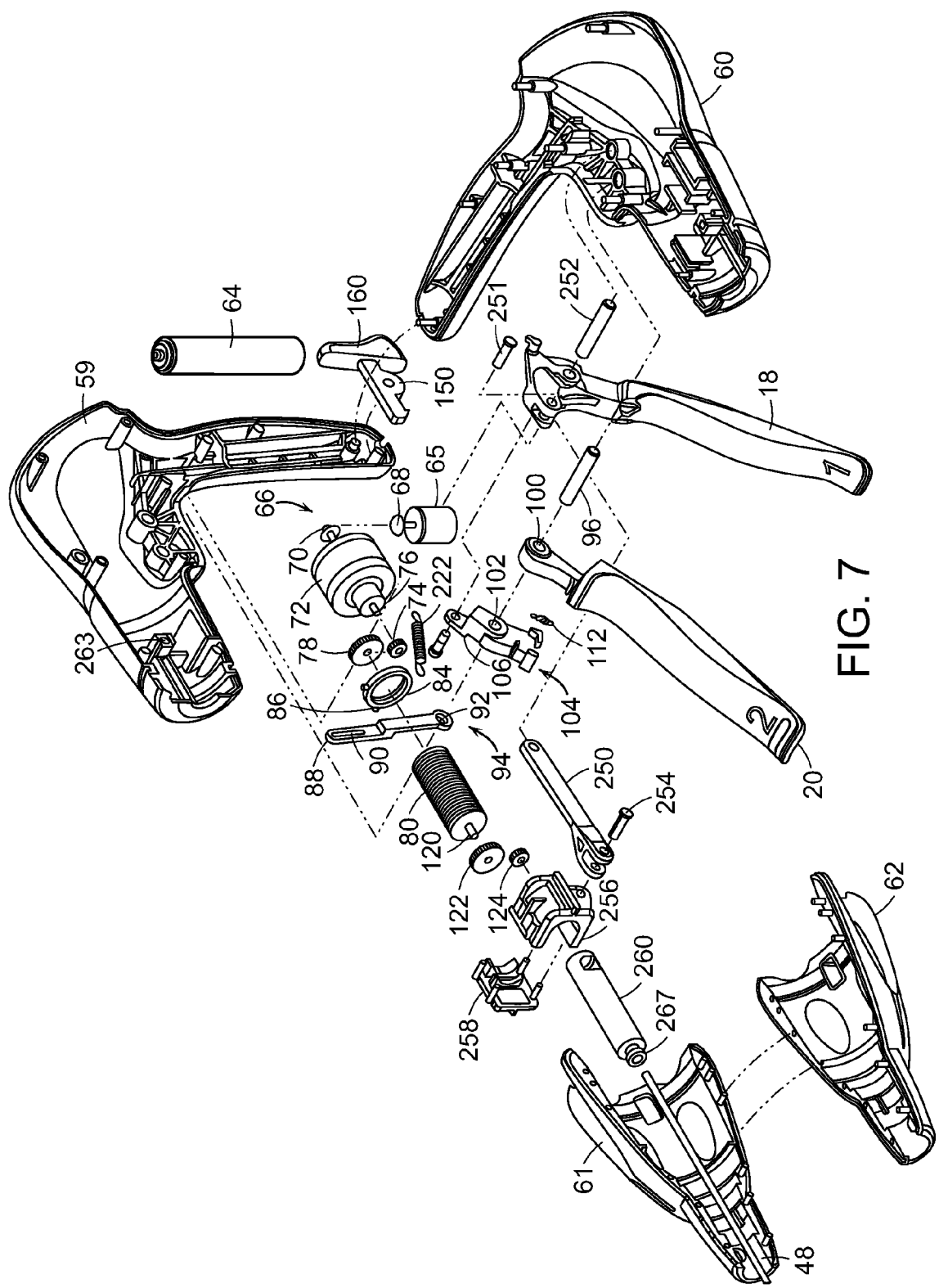
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

In addition, according to various embodiments, the instrument 10 may comprise a cutting instrument position sensor 150 that senses the position of the cutting instrument 32 within the staple channel 22. In one embodiment, the cutting instrument position sensor 150 may comprises an encoder positioned to sense rotation of the helical screw shaft 36, or any other drive shaft or gear whose rotation is related to the position of the knife 32 in the end effector 12. Because the rotation of the shaft 36 or other drive shafts/gears is proportional to the movement of the cutting instrument 32 along the length of the channel 22, the signal generated by the encoder 150 is also proportional to the movement of the cutting instrument 32 in the channel 22.

FIGS. 7-10 illustrate an exemplary embodiment of a motor-driven endocutter. The illustrated embodiment provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower sidepieces 59, 60 and exterior upper side pieces 61, 62 that fit together to form, in general, the exterior of the handle 6. A battery (or "power source" or "power pack") 64, such as a Li ion battery, may be provided in the pistol grip portion 26 of the handle 6. The battery 64 powers an electric motor 65 disposed in an upper portion of the pistol grip portion 26 of the handle 6. According to various embodiments, a number of battery cells connected in series may be used to power the motor 65. In addition, the power source 64 may be replaceable and/or rechargeable.

The motor 65 may be a DC brushed driving motor having a maximum rotation of, approximately, 25,000 RPM. In other embodiments, the motor 65 may include a brushless motor, a cordless motor, a synchronous motor, a stepper motor, or any other suitable electric motor. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72, and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and complete the circuit used to power the motor 65. When the sensor 110 is a variable resistor or the like, the current supplied to the motor 65, and hence the output torque of the motor 65, may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation. In other embodiments, the sensor 110 may be an on-off type switch. In such an embodiment, when the firing trigger 20 is retracted, the sensor switch 110 is closed, thereby completing the circuit used to power the motor 65.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to remove thereby force from the sensor 100, to stop thereby the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130 may be part of the circuit used to control the motor 65. When the reverse motor sensor is activated, the motor control circuit may reverse the direction of the motor 65, thereby withdrawing the knife 32 of the end effector 12 following the cutting operation. The stop motor sensor 142 may be, for example, a normally closed limit switch, and may also be part of the motor control circuit. In various embodiments, it may be located at the proximate end of the helical gear drum 80 so that the ring 84 trips the switch 142 when the ring 84 reaches the proximate end of the helical gear drum 80, indicating that the cutting instrument 32 has reached its proximate (or home or initial) position in the end effector 12.

In operation, when an operator of the instrument 10 pulls back the firing trigger 20, the sensor 110 detects the deployment of the firing trigger 20 and the motor control circuit causes the motor 65 to forward rotate at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which causes the motor control circuit to reverse the direction of the motor 65. This in turn causes the knife 32 to retract, and also causes the ring 84 on the helical gear drum 80 to move back to the proximate end of the helical gear drum 80.

Figure 8:
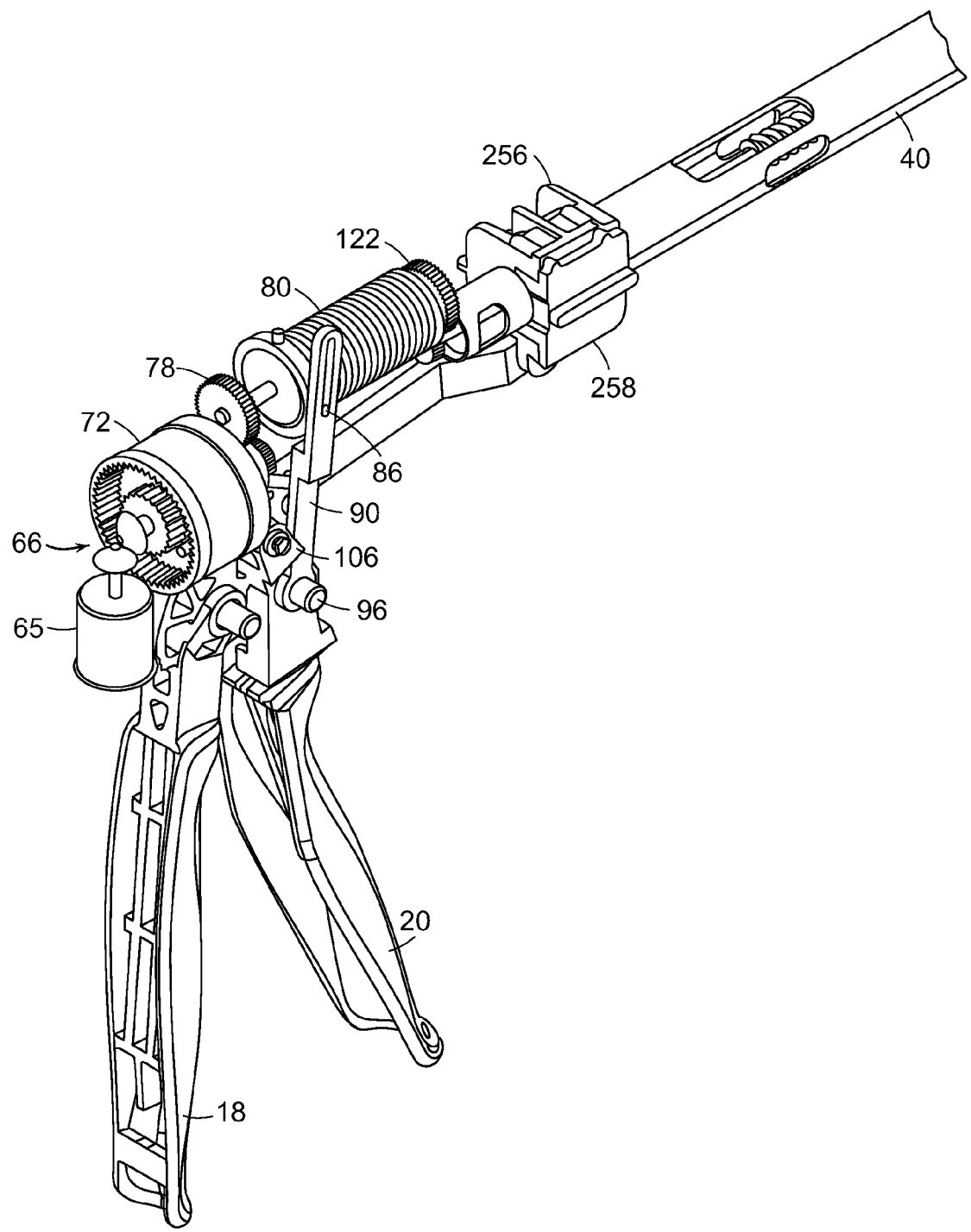
FIGS. 8 and 9 are partial perspective views of the handle according to various embodiments of the present invention.
Figure 9:
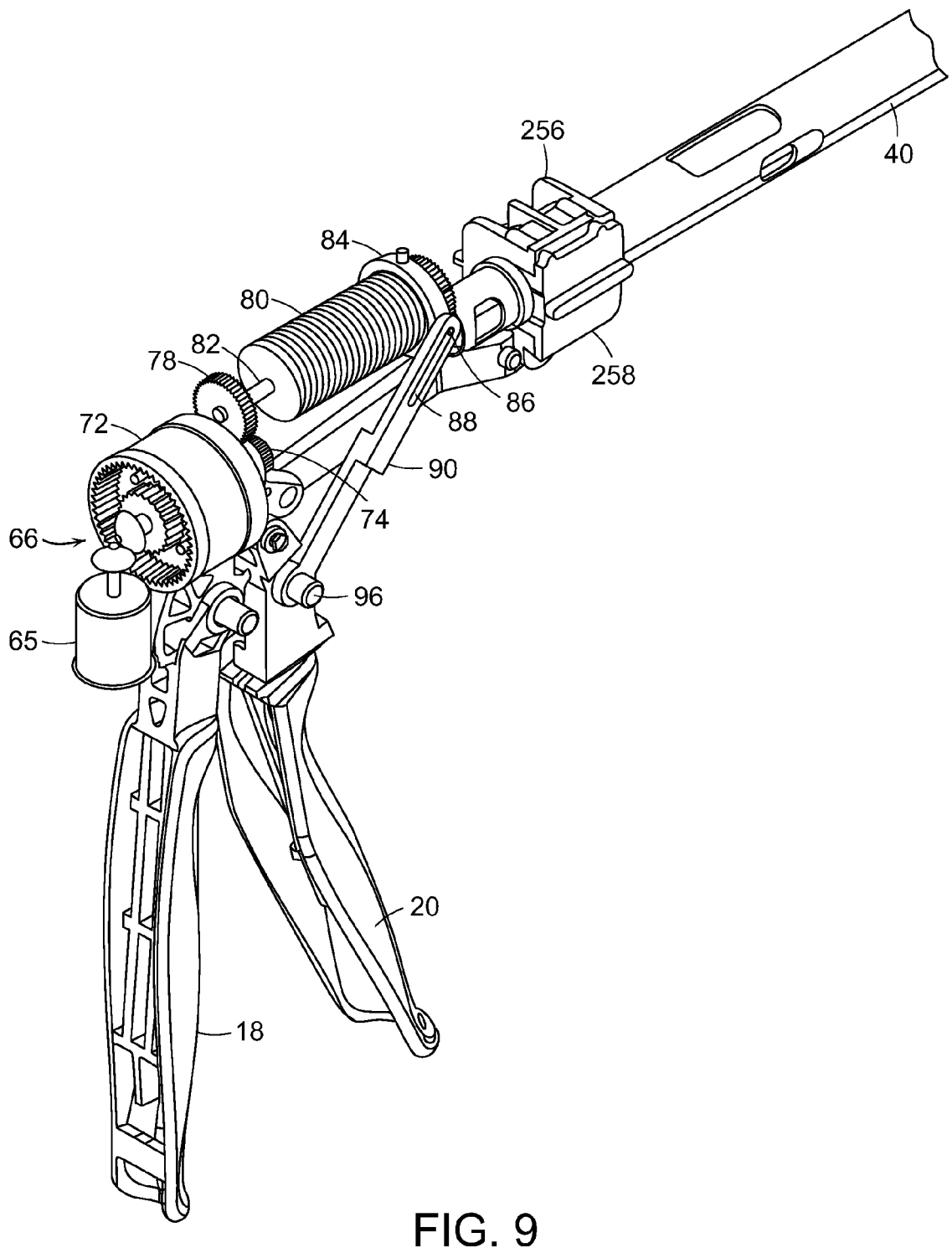
Figure 10:
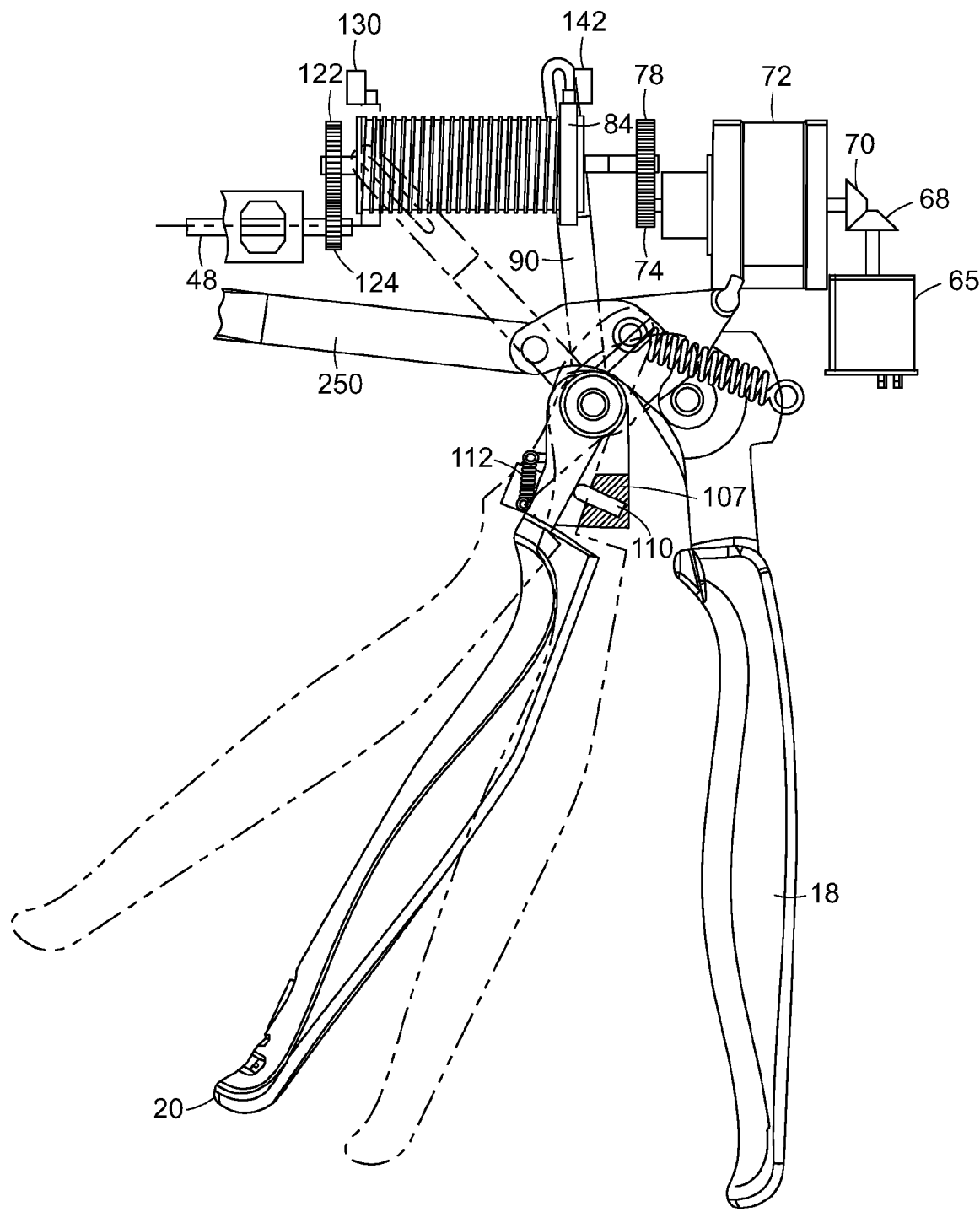
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower sidepiece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Additional configurations for motorized surgical instruments are disclosed in published U.S. application Pub. No. 2007/0175962 A1, entitled "Motor-driven surgical cutting and fastening instrument with tactile position feedback," which is incorporated herein by reference in its entirety.

Figure 11:
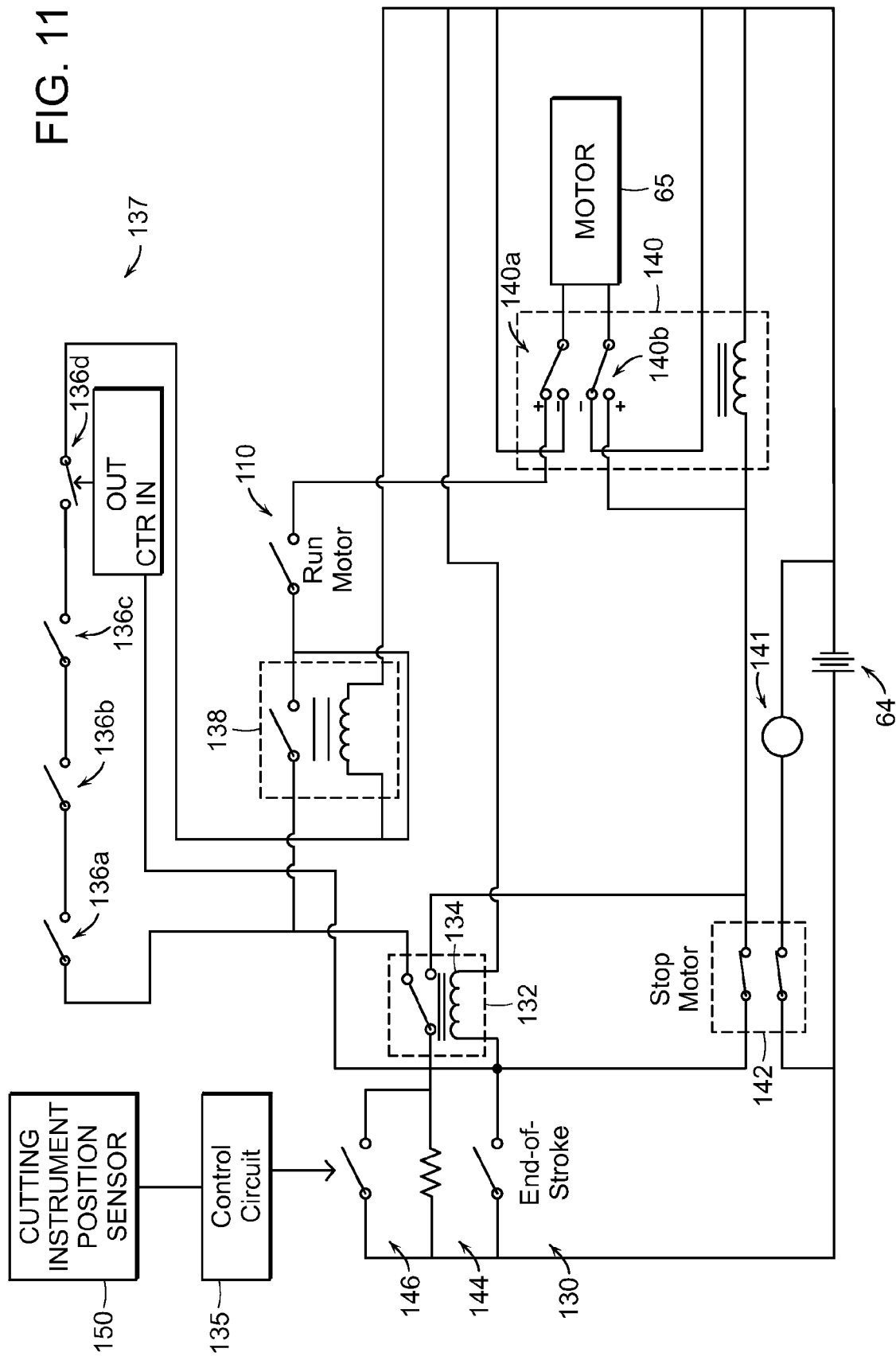

FIG. 11 is a schematic diagram of the motor control circuit according to various embodiments of the present invention. In various embodiments, the motor control circuit may include one of more integrated circuits (ICs), such as, for example, a processor, memory, microcontroller, time circuits, etc. In other embodiments, the motor control circuit may not comprise any ICs. Such a non-IC motor control circuit may be advantageous because it is often difficult, complicated, and expensive to sterilize a surgical instrument including ICs.

When an operator initially pulls in the firing trigger 20 after locking the closure trigger 18, the sensor 110 is activated (or closed, where the sensor 110 is a switch), allowing current to flow therethrough. If the normally open reverse motor sensor switch 130 is open (meaning the end of the end effector stroke has not been reached), current will flow to a single pole, double throw relay 132. When the reverse motor sensor switch 130 is not closed, a coil 134 of the relay 132 will not be energized, so the relay 132 will be in its de-energized state.

As shown in FIG. 11, the circuit may also include a resistive element 144 and a switch 146 connected in parallel, with the paralleled elements connected in series with the relay 132. The resistive element 144 and the switch 146 are also connected to the power source 64. The switch 146 may be controlled by a control circuit 148 that is responsive to the cutting instrument position sensor 150. According to various embodiments, the control circuit 148 may open the switch 146 when the cutting instrument 32 is (i) very near to the beginning of its stroke and (ii) very near to the end of its stroke. For example, the control circuit may open the switch when the cutting instrument 32 is (i) 0.001 inches from the beginning point of its stroke and (ii) 0.001 inches from the end of its stroke, as determined by the cutting instrument position sensor 150. With the switch 146 open, current flows through the resistive element 144, and then through the relay 132, the relay 138, the run motor sensor switch 110, to the motor 65. Current flowing through the resistive element 144 reduces the magnitude of the current delivered to the motor 65, thereby reducing the power delivered by the motor 65. Thus, when the cutting instrument 32 is (i) very near to the beginning of its stroke or (ii) very near to the end of its stroke, the power delivered by the motor 65 is reduced. Conversely, once the cutting instrument 32 moves sufficiently far from its beginning point or end of stroke point, the control circuit 148 may close the switch 146, thereby shorting the resistive element 144, thereby increasing the current to the motor 65, thereby increasing the power delivered by the motor.

According to various embodiments, the electrical circuit further includes lockout sensor switches 136a-d collectively defining an interlock circuit 137 through which current from the relay 132, when de-energized, passes in order for electrical operation of the motor 65 to be initiated. Each lockout sensor switch 136a-d may be configured to maintain an open (i.e., non-conductive) switch state or a closed (i.e., conductive) switch state responsive to the presence or absence, respectively, of a corresponding condition. Any of the corresponding conditions, if present when the instrument 10 is fired, may result in an unsatisfactory cutting and stapling operation and/or damage to the instrument 10. Conditions to which the lockout sensor switches 136a-d may respond include, for example, (a) the absence of the staple cartridge 34 in the channel 22, (b) the presence of a spent (e.g., previously fired) staple cartridge 34 in the channel 22, and (c) an open (or otherwise insufficiently closed) position of the anvil 24 with respect to the channel 22. Other conditions to which the lockout sensor switches 136a-d may respond, such as component wear, may be inferred based upon an accumulated number of firing operations produced by the instrument 10. Accordingly, in various embodiments, if any of these conditions exists, the corresponding lockout sensor switches 136a-d maintain an open switch state, thus preventing passage of the current necessary to initiate operation of the motor 65. Passage of current by the lockout sensors 136a-d is allowed, in various embodiments, only after all of the conditions have been remedied. It will be appreciated that the above-described conditions are provided by way of example only, and that additional lockout sensor switches for responding to other conditions detrimental to operation of the instrument 10 may be provided. It will similarly be appreciated that for embodiments in which one or more of the above-described conditions may not exist or are of no concern, the number of lockout sensor switches may be fewer than that depicted.

As shown in FIG. 11, the lockout sensor switch 136a may be implemented using a normally open switch configuration such that a closed switch state is maintained when the staple cartridge 34 is in a position corresponding to its proper receipt by the channel 22. When the staple cartridge 34 is not installed in the channel 22, or is installed improperly (e.g., mis-aligned), the lockout sensor switch 136a maintains an open switch state. Lockout sensor switch 136b may be implemented using a normally open switch configuration such that a closed switch state is maintained only when an unspent staple cartridge 34 (i.e., a staple cartridge 34 having a sled 33 in the unfired position) is present in the channel 22. The presence of a spent staple cartridge 34 in the channel 22 causes the lockout sensor switch 136b to maintain an open switch state. Lockout sensor switch 136c may be implemented using a normally open switch configuration such that a closed switch state is maintained when the anvil 24 is in a closed position with respect to the channel 22. The lockout sensor switch 136c may be controlled in accordance with a time delay feature wherein a closed switch state is maintained only after the anvil 24 is in the closed position for a pre-determined period of time.

Lockout sensor switch 136d may be implemented using a normally closed switch configuration such that a closed switch state is maintained only when an accumulated number of firings produced by the instrument 10 is less than a pre-determined number. The lockout sensor switch 136d may be in communication with a counter 139 configured for maintaining a count representative of the accumulated number of firing operations performed by the instrument 10, comparing the count to the pre-determined number, and controlling the switch state of the lockout sensor switch 136d based upon the comparison. Although shown separately in FIG. 11, it will be appreciated that counter 139 may be integral with the lockout sensor switch 136d so as to form a common device. Preferably, the counter 139 is implemented as an electronic device having an input for incrementing the maintained count based upon the transition of a discrete electrical signal provided thereto. It will be appreciated that a mechanical counter configured for maintaining the count based upon a mechanical input (e.g., retraction of the firing trigger 20) may be used instead. When implemented as an electronic device, any discrete signal present in the electrical circuit that transitions once for each firing operation may be utilized for the counter 139 input. As shown in FIG. 11, for example, the discrete electrical signal resulting from actuation of the end-of-stroke sensor 130 may be utilized. The counter 139 may control the switch state of lockout sensor switch 136d such that a closed switch state is maintained when the maintained count is less than a pre-determined number stored within the counter 139. When the maintained count is equal to the pre-determined number, the counter 139 causes the lockout sensor switch 136d to maintain an open switch state, thus preventing the passage of current therethrough. It will be appreciated that the pre-determined number stored by the counter 139 may be selectively adjusted as required. According to various embodiments, the counter 304 may be in communication with an external display (not shown), such as an LCD display, integral to the instrument 10 for indicating to a user either the maintained count or the difference between the pre-determined number and the maintained count.

According to various embodiments, the interlock circuit 137 may comprise one or more indicators visible to the user of the instrument 10 for displaying a status of at least one of the lockout sensor switches 136a-d. More details regarding such indicators may be found in published U.S. patent application Pub. No. 2007/0175956, entitled "Electronic lockouts and surgical instrument including same," which is incorporated herein by reference in its entirety. This application also includes example mounting arrangements and configurations for the lockout sensor switches 136a-d.

In the illustrated embodiment, when the lockout sensor switches 136a-d collectively maintain a closed switch state, a single pole, single throw relay 138 is energized. When the relay 138 is energized, current flows through the relay 138, through the run motor switch sensor 110, and to the motor 65 via a double pole, double throw relay 140, thereby powering the motor 65, allowing it to rotate in the forward direction. According to various embodiments, because the output of the relay 138, once energized, maintains the relay 138 in an energized state until relay 132 is energized, the interlock circuit 137 will not function to prevent operation of the motor 165 once initiated, even if one or more of the interlock sensor switches 136a-d subsequently maintains an open switch state. In other embodiments, however, it may be necessary or otherwise desirable to connect the interlock circuit 137 and the relay 138 such that one or more the lockout sensor switches 136a-d must maintain a closed switch state in order to sustain operation of the motor 165 once initiated.

Rotation of the motor in the forward direction causes the ring 84 to move distally and thereby de-actuate the stop motor sensor switch 142 in various embodiments. Because the switch 142 is normally closed, a solenoid 141 connected to the switch 142 may be energized. The solenoid 141 may be a conventional push-type solenoid that, when energized, causes a plunger (not shown) to be axially extended. Extension of the plunger may operate to retain the closure trigger 18 in the retracted position, thus preventing the anvil 24 from opening while a firing operation is in progress (i.e., while the switch 142 is not actuated). Upon de-energization of the solenoid 141, the plunger is retracted such that manual release of the closure trigger 18 is possible.

When the end effector 12 reaches the end of its stroke, the reverse motor sensor 130 will be activated, thereby closing the switch 130 and energizing the relay 132. This causes the relay 132 to assume its energized state (not shown in FIG. 11), which causes current to bypass the interlock circuit 137 and run motor sensor switch 110, and instead causes current to flow to both the normally-closed double pole, double throw relay 140 and back to the motor 65, but in a manner, via the relay 140, that causes the motor 65 to reverse its rotational direction. Because the stop motor sensor switch 142 is normally closed, current will flow back to the relay 132 to keep it energized until the switch 142 opens. When the knife 32 is fully retracted, the stop motor sensor switch 142 is activated, causing the switch 142 to open, thereby removing power from the motor 65, and de-energizing the solenoid 141.

FIG. 12 illustrates a timeline of the operation of the circuit according to various embodiments Assuming the lockout switches 136*a*-*d* are in their appropriate state, at time T0 the operator retracts the firing trigger 20, closing the run motor sensor switch 110, causing the motor 65 to forward rotate. At this time, the switch 146 is open, so current flows through the resistive element 144, reducing the current to the motor 65 from time T0 to time T1. At time T1, which the cutting instrument is sufficiently far from its initial position, the switch 146 is closed, thereby shorting the resistive element 144 and supplying increased power to the motor 65. From time T1 to time T2, the motor is in its full power mode with the switch 146 closed. At time T2, as the cutting instrument 32 gets near to the end of its stroke, the switch 146 is opened, thereby reducing the current supplied to the motor 65. Thus, from T2 to T3 the motor 65 is at less than full power.

At time T3, the end-of-stroke sensor switch 130 is closed, causing the motor 65 to reverse rotate. The motor 65 is still in its reduced power state because switch 146 is opened, and the motor 65 remains in its reduced power state until time T4, when the switch 146 is closed because the cutting instrument 32 has moved sufficiently far from its end-of-stroke position. From time T4 to T5 the motor 65 operates at full power retracting the cutting instrument 32. At time T5, as the cutting instrument 32 gets near to its initial (or stop) position, the switch 146 again opens, thereby limiting current to the power 65, thereby reducing the power delivered by the motor 65. At time T6, the stop motor sensor switch 142 is opened, thereby removing current from the motor, causing it to stop rotating.

In such a switching architecture, the motor-driven instrument 10 exhibits a "soft" start quality by limiting the motor's ability to exert full load immediately. The motor 65 is initially in a reduced power mode (from time T0 to time T1), so as to limit the sudden jerking start. In addition, by starting the soft start mode, the likelihood of the motor overpowering the cartridge lockout mechanism is reduced. In addition, reducing the power prior to the knife reaching its end-of-stroke (or distal) position eases reversal of the motor direction.

In other embodiments, the parallel-connected switch 146 and resistive element 144 are connected in different places, but preferably they are always in the current loop regardless of whether the motor 65 is being forward rotated or reverse rotated. In addition, the resistive element 144 may be any type of circuit element or electrical component that provides sufficient resistance. For example, the resistive element 144 could be one or a number of parallel-connected resistors.

Figure 13:
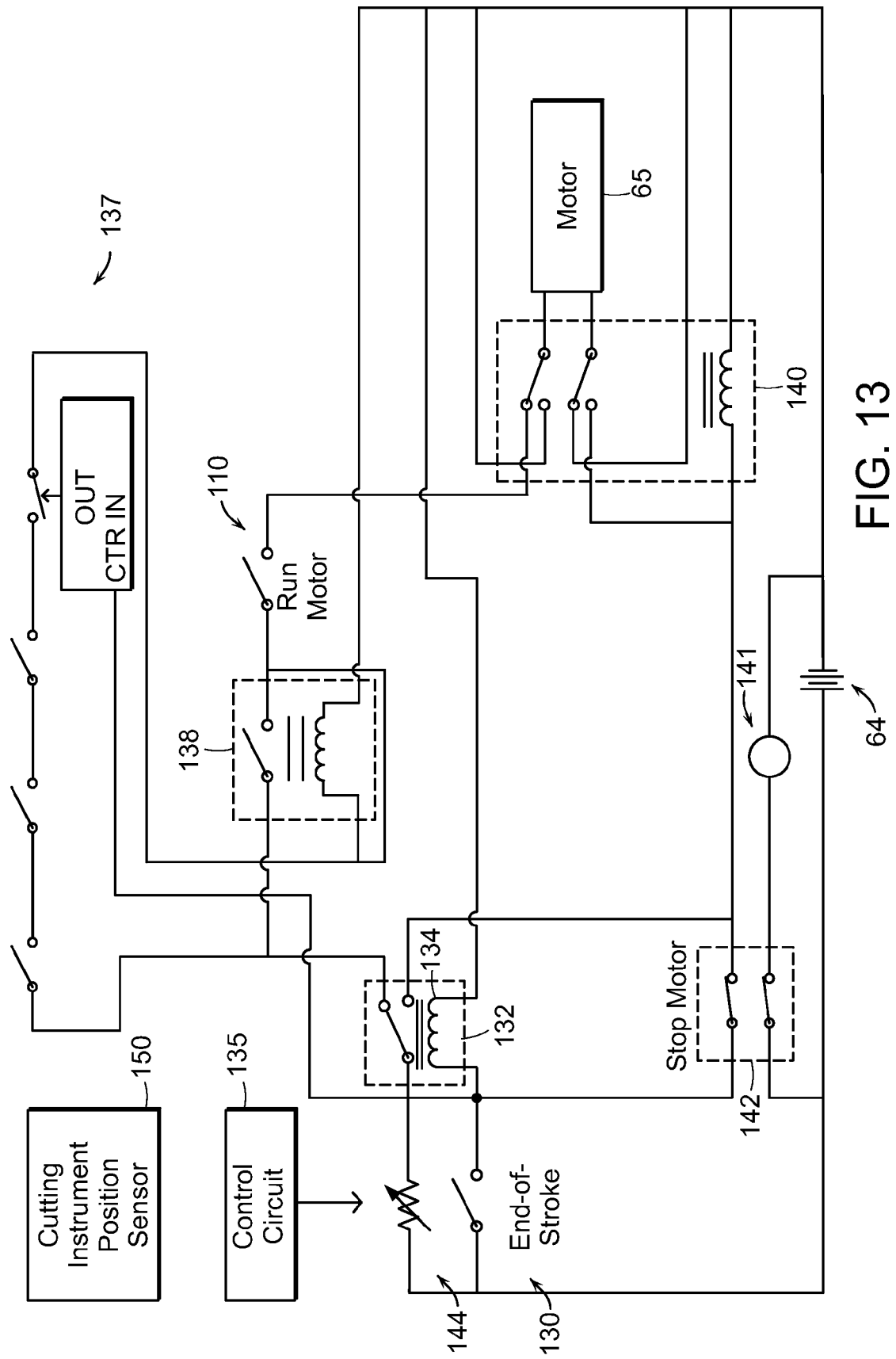
Figure 14:
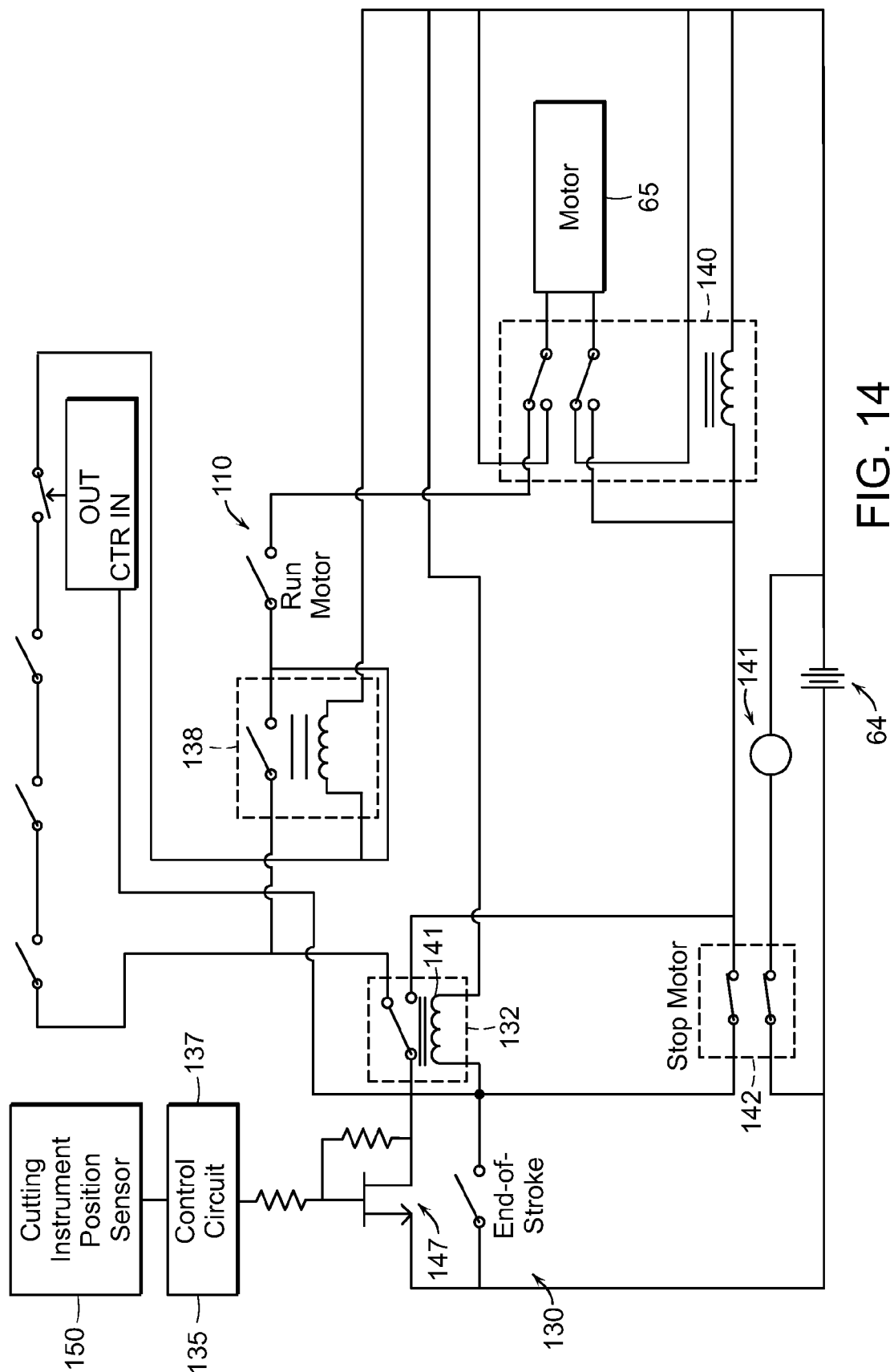

In addition, the resistive element 144 may comprise a variable resistor, as shown in FIG. 13. In such an embodiment, the switch 146 may or may not be used. FIG. 13 shows an embodiment without the switch 146. The control circuit 148 may vary the resistance of the variable resistive element 144 based on the position of the cutting instrument 32, for example. That way, instead of having two power levels for the motor 65, there could be a number of discrete power levels or a continuous range of power levels for the motor 65, depending on the nature of the variable resistive element 144. In various embodiments, the variable resistive element may comprise a string potentiometer or cable position transducer, where, for example, the resistance is related to the position of the knife 32 in the end effector 12. In addition, an active element, such as a transistor, could be used to provide a variable resistance. For example, FIG. 14 illustrates a circuit where a FET 147 is used as a variable resistor to limit the current to the motor 65 in various operational states.

Figure 15:
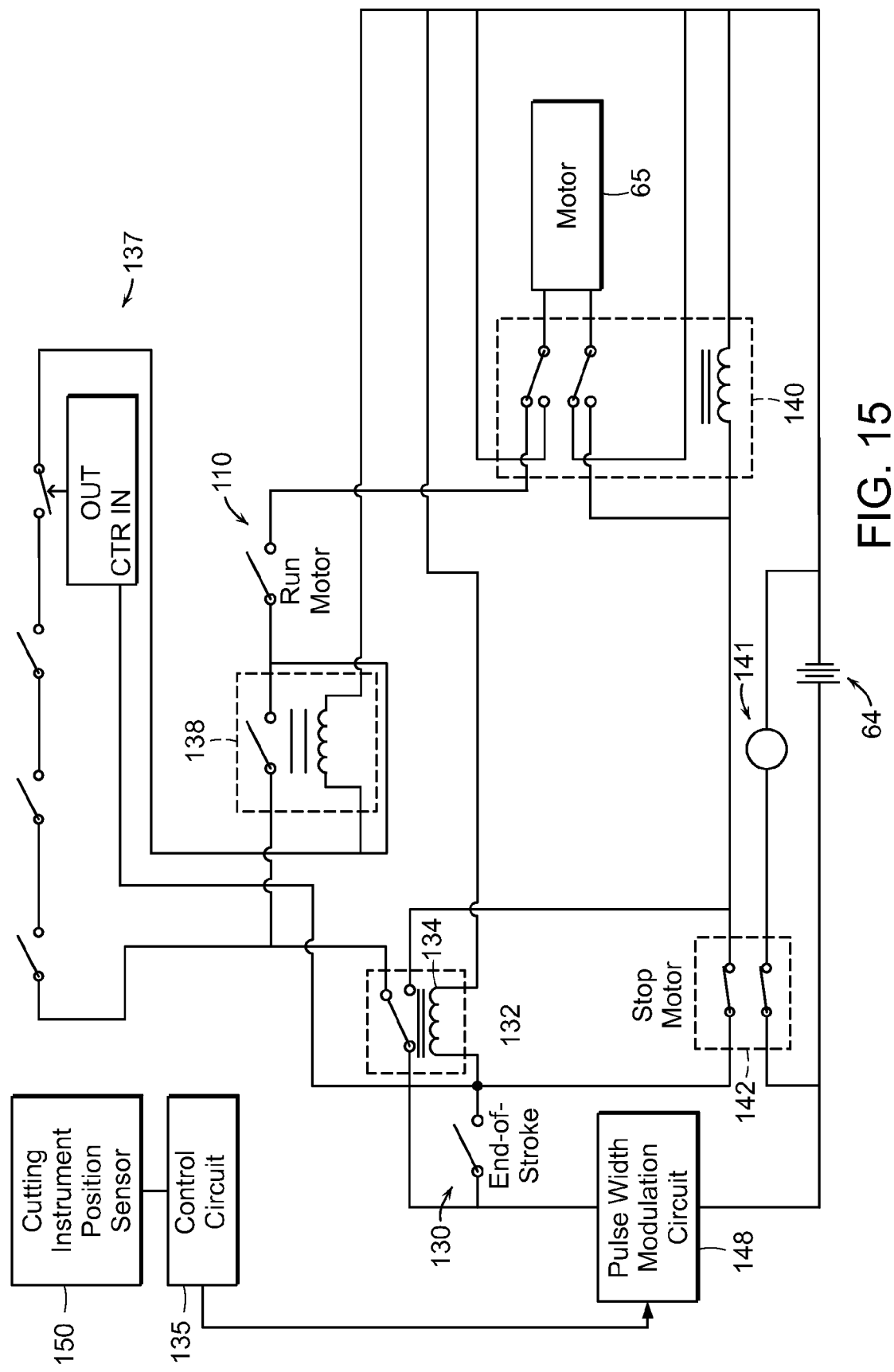
Figure 16:
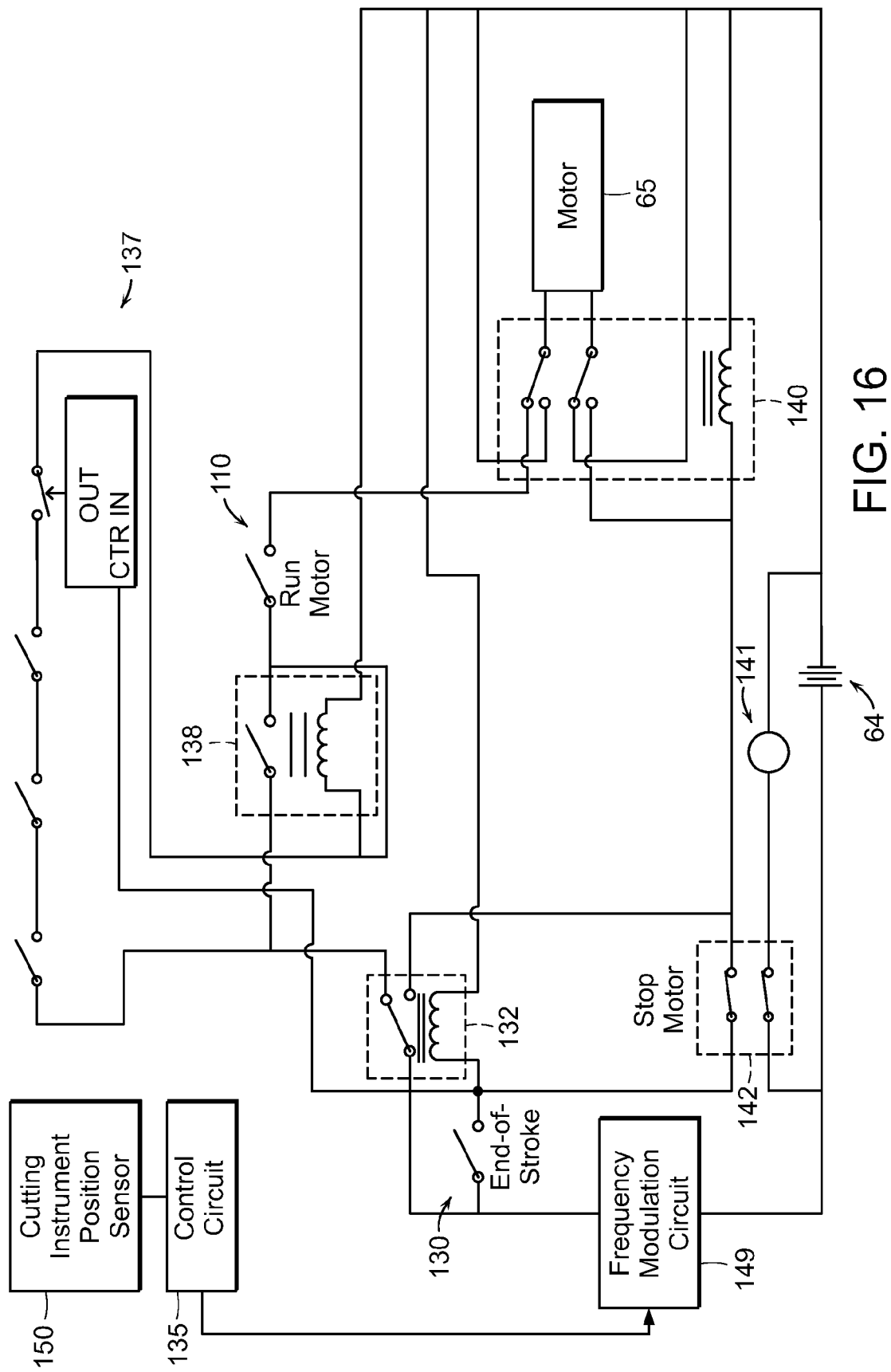

In yet other embodiments, an integrated switch mode controller, such as the UC2637 from Texas Instrument or some other suitable motor drive circuit, could be used to limit the torque and/or speed of the motor 65 at various times during the cutting stroke cycle, such as a "soft" start, within the lockout region, prior to stopping or reversing direction, etc. According to yet other embodiments, as shown in FIG. 15, a pulse width modulation circuit 148 may be used to control the speed of the motor 65 by driving the motor with short pulses. The duration of the pulses may be varied to control the speed of the motor 65; the longer the pulses, the faster the motor turns, and vice versa. Accordingly, short duration pulses may be used when the cutting instrument 32 is initially leaving or returning to its initial position, or approaching or leaving its end-of-stroke position, etc. In addition, in yet other embodiments, a frequency modulation circuit 149, as shown in FIG. 16, may be used to control the speed of the motor 65. In a frequency modulation circuit, the duty cycle of the pulse remains constant, but the frequency of the pulses changes to vary the speed of the motor. Accordingly, low frequency pulses may be used when the cutting instrument 32 is initially leaving or returning to its initial position, or approaching or leaving its end-of-stroke position, etc., and high frequency pulses may be used when greater motor speed is required.

Figure 17:
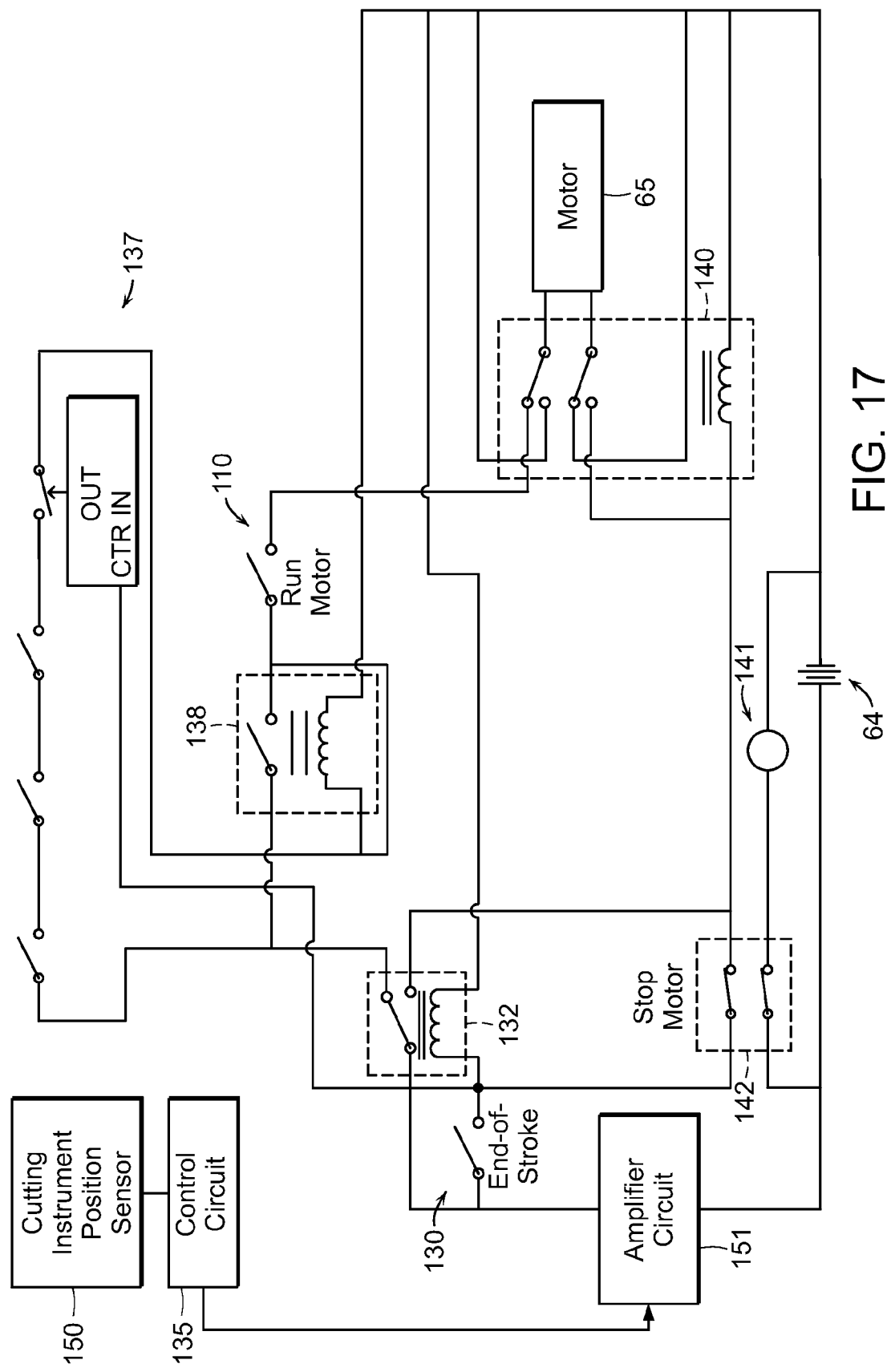

In yet other embodiments, an amplifier circuit 151 may be used to control the speed of the motor 65, as shown in FIG. 17. The amplifier circuit 151 may amplify, for example, the current or voltage applied to the motor 65. According to various embodiments, the amplifier circuit 151 may comprise a Darlington transistor pair or some other suitable transistor-based amplifier circuit.

In other embodiments, rather than an on-off type run motor sensor switch 110, a proportional-type variable resistor sensor could be used instead. In such embodiments, the rate of rotation of the motor 65 would be proportional to the force applied by the operator. The run-motor sensor 110 may provide an open circuit resistance when the firing trigger 20 is not retracted/actuated, and then provide a decreasing resistance as the firing trigger is retracted. Whether the switch 110 comprises an on-off type switch or a variable resistor, if the operator releases the firing trigger 20 during a procedure while the motor is in the forward direction, power to the motor 65 will be eliminated or at least reduced, thereby providing a dynamic braking feature for the instrument 10.

Figure 18:
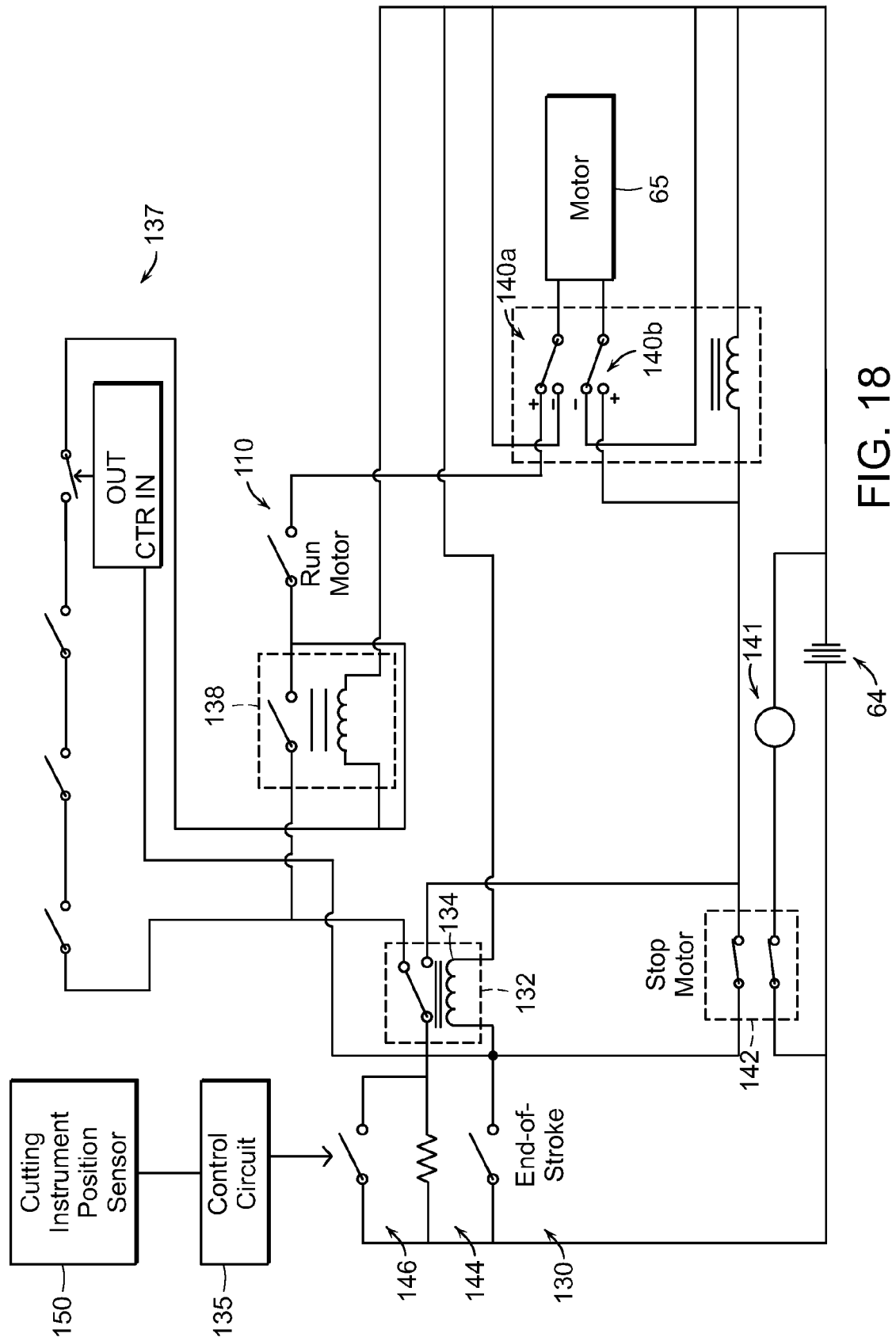

In other embodiments, as shown in FIG. 18, the switches 140*a* and 140*b* may be actively controlled, rather than through the relay 140 shown in FIG. 11, for example. In such embodiments, just before the end of the stroke is sensed, one of the switches 140*a*, 140*b* may switch polarity so that both switches 140*a*, 140*b* are connected to the same polarity terminal for the motor 65 (e.g., either both positive or both negative). This will remove power from the motor 65, causing it to stop. FIG. 18 shows an embodiment where the switches 104*a* and 140*b* are both connected to the positive terminal. Then, at about the same time the end-of stroke is sensed or soon thereafter, the other switch 140*a*, 140*b* may switch polarity, allowing the motor 65 to rotate in the reverse direction. In the example of FIG. 18, this may be done by switching switch 140a to the negative terminal. Of course, in other embodiments, the switch 140a could be first switched to the negative terminal and then the switch 140b could be switched to the positive terminal. Also, other switching arrangements could be used to temporarily remove power from the motor 65 prior to it switching direction to provide such "active braking." For example, the switches 140a, 140b may still be controlled by an inductive relay, and the circuit may include another switching circuit for actively braking the motor 65.

The active braking could be combined with variable power levels supplied to the motor 65 as described above in connection with FIGS. 11 and 12, for example. FIG. 19 shows a timing diagram that incorporates active braking. At time T2.1, between times T2 and T3, the power may be removed from the motor 65 by switching one of the switches 140a, 104b, for example, thereby braking the motor. Then at time T3, the end-of-stroke switch 130 may be closed and the other switch 140a, 140b may be switched to supply power to the motor 65, but in the reverse direction, as described above.

The control circuit 135 or some other control circuit may control the switching of the switches 140a, 140b. According to various embodiments, the control circuit 135 may comprise a processor and memory. For example, the control circuit 135 may comprise an IC-based microcontroller. The memory may store data indicative of the type of cartridge 34 loaded in the end effector 12. For example, the memory may store data indicative of the length of the cut needed for the cartridge 34. Based on this data, the control circuit 135 can control when the switches 146, 140a, and 140b switch. As the cartridges 34 are often replaceable in certain types of instruments 10, the identifying data may be transmitted to the control circuit 135 by a RFID tag or transponder connected to or associated with the cartridge 34 or by some other means. The RFID signal from the tag may be received by the control circuit 135 and stored in memory. In other embodiments, a transponder associated with the cartridge 34 may send identifying data to the control circuit 135 via one or more inductive links, such as described in published U.S. patent application Pub. No. 2008/0167522, entitled "Surgical instrument with wireless communication between control unit and sensor transponders," which is incorporated herein by reference in its entirety.

According to other embodiments, the control circuit 135 may not contain any integrated circuits. For example, the control circuit 135 may comprise analog timer circuits (e.g., RC-based timer circuits) for controlling the switch timing of the switches 146, 140a-b. According to such an embodiment, the control circuit 135 may receive information about the length of the cut for the particular cartridge 34 being used based on the completion of an electrical circuit when the cartridge 34 is inserted into the channel 22. For example, as shown in FIG. 20, the channel 22 may comprise a number of contact pads 220 positioned to face the lower surface of the cartridge 34 when the cartridge 34 is loaded in the channel 22. The lower surface of the cartridge 34 also may comprise a number of contacts 222, as shown in FIG. 21. The number and positioning of the contacts 222 on the cartridge 34 may identify the type of cartridge. For example, the number and positioning of the contacts 222 may identify the cut length for the cartridge 34. All cartridges of the same cut length would preferably have the same contact pattern; cartridges with different cut lengths would have different contact patterns. The circuit completed when the contacts 222 of the cartridge 34 contact the contacts 220 of the channel 22 may have a number of different resistors, a subset of which are connected in the completed circuit when the contacts 222 of the cartridge 34 contact the contacts 220 of the channel 22. Depending on the contact pattern on the cartridge 34, different resistors may be in the completed circuit. The resistors may be connected to the control circuit 135, and may be used in the RC circuits to generate the timing signals for the switches 146, 140a, 140b. That way, the control circuit 135 can control the switches 146, 140a-b based on the type of cartridge 34 loaded in the end effector 12.

In another embodiment, the lower surface of the cartridge 34 may comprise a plunger 230, as shown in FIG. 22. The channel 22 may comprise a number of switches 232, as shown in FIG. 23, one of which is actuated by the plunger 230 when the cartridge 34 is loaded in the end effector 12. The switch 232 may have a different associated resistor circuit. Each of the resistor circuits may be connected to the control circuit 135, but only one would be activated when the cartridge 34 is loaded in the channel 22, depending on the location of the plunger 230. Each replaceable cartridge 34 having the same cut length preferably would have the plunger 230 in the same position. Cartridges 34 with different lengths would preferably have plungers 230 in different positions. Because the end effector 12 may only accommodate a finite number of different cartridges (e.g., 5), the channel 22 would only need a corresponding number of switches 232 and there would only be a corresponding number of acceptable plunger locations.

Figure 24:
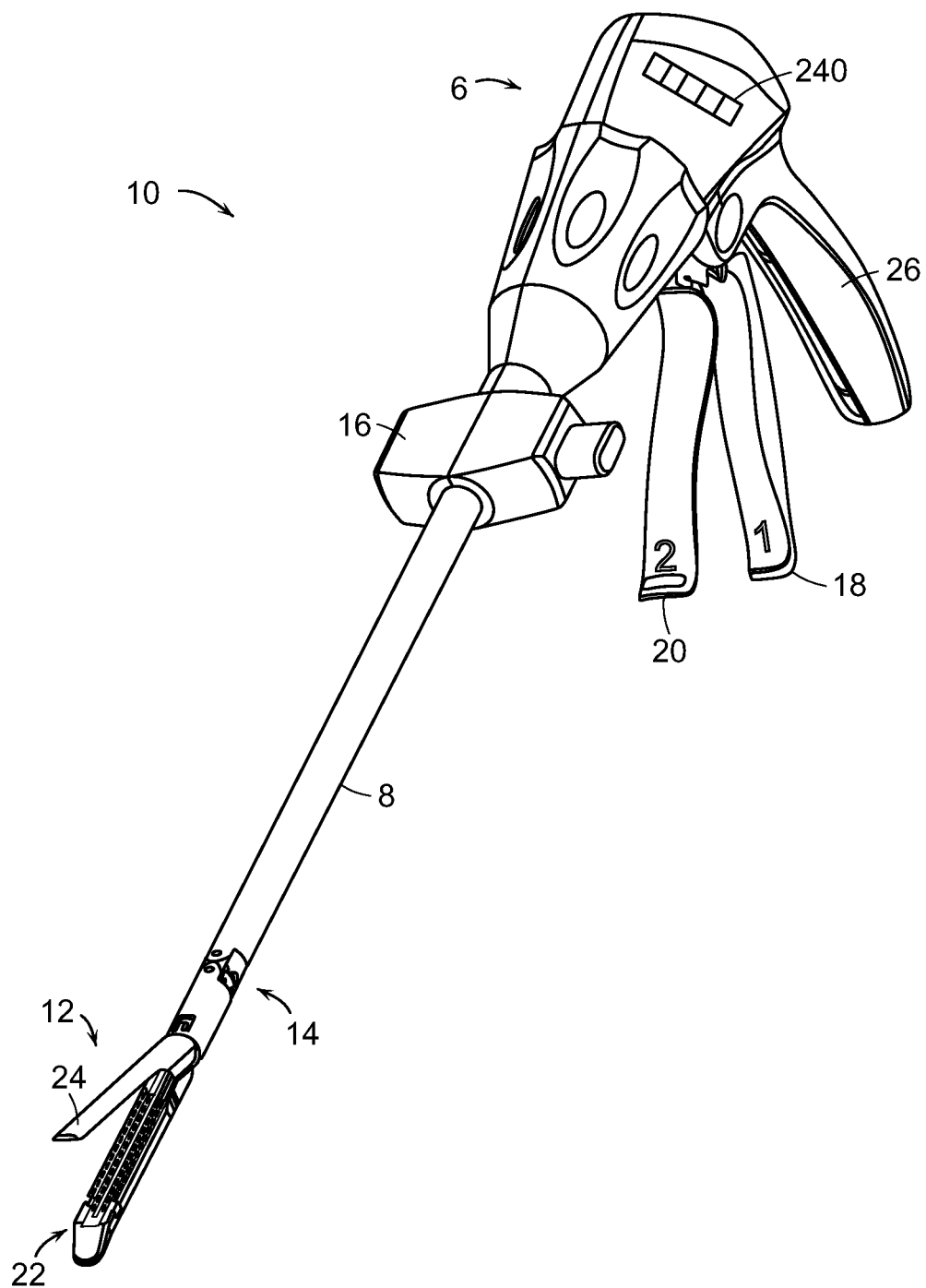

In other embodiments, the instrument 10 may comprise an external selector 240, such as dip switch or other suitable input device, whereby an operator of the instrument or other person could input identifying data for the cartridge 34 being used. As shown in FIG. 24, the handle may comprise such a selector 240 for embodiments where the control circuit 135 comprises an IC or embodiments where the control circuit 135 does not comprise any ICs.

Figure 25:
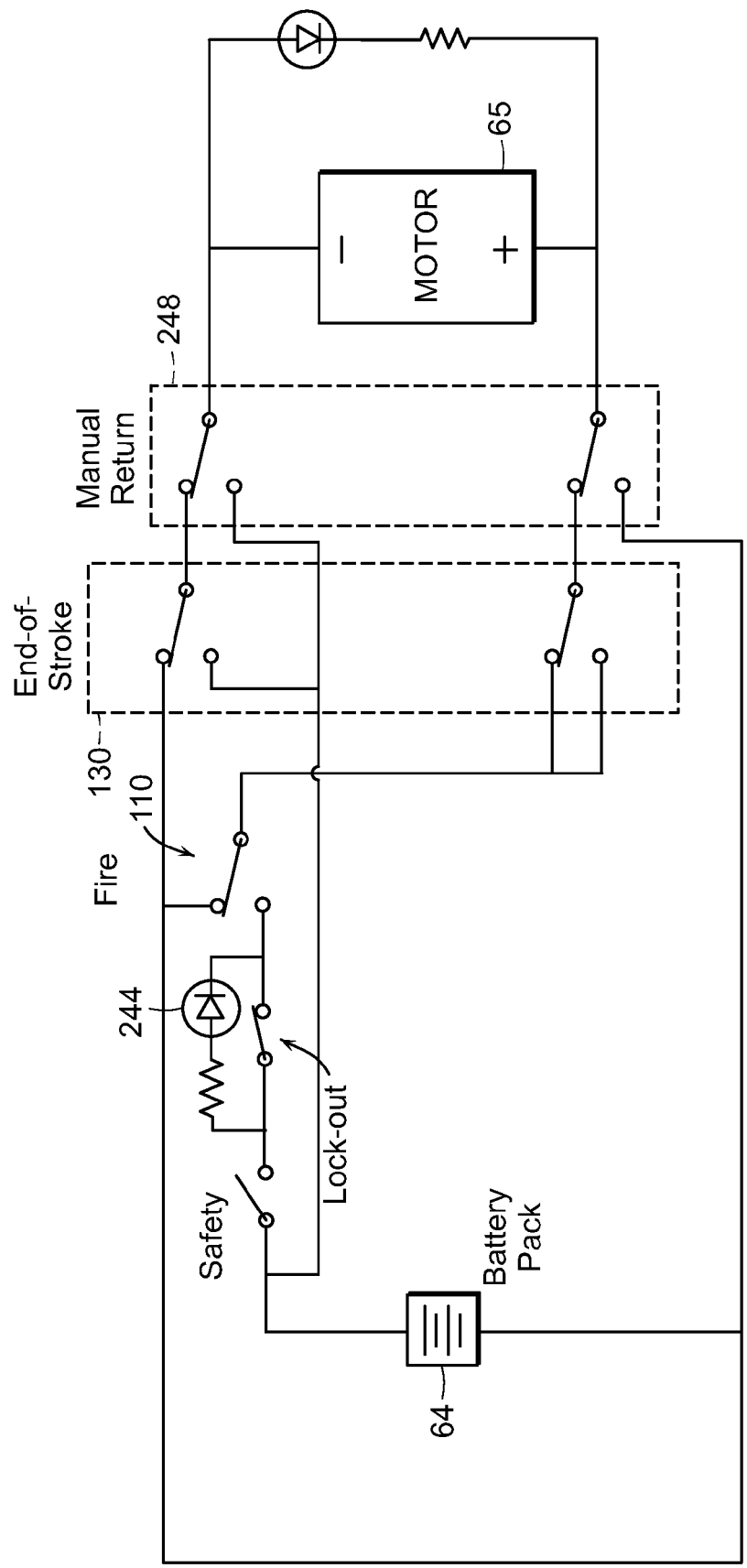

FIG. 25 shows another embodiment of the motor circuit. When the run motor (or fire) switch 110 is closed (it is shown in an open state in FIG. 25), when the safety switch 240 is closed (it is shown open in FIG. 25) indicating that the device safety is set, and when the normally-closed lockout switch 242 it opened indicating that the instrument is not in a lock-out condition, current flows through the safety switch 240, through the lockout indicator 244 (which may be a LED as shown in FIG. 25) to the motor 65. When the end of the cutting stroke is reached, the end-of-stroke or direction switch 130 is switched, reversing the direction of the motor 65 (with the fire switch 110 also having been released). In this state, current also flows through a reverse direction indicator 246, such as an LED, providing a visual indication that the motor direction has been reversed.

As shown in FIG. 25, the circuit may also comprise a manual return switch 248. The operator may manually flip this switch if the cutting instrument 32 has only been partially fired. Switching the manual return switch 248 causes the motor 65 to reverse rotate, causing the cutting instrument 32 to return to its original or home position.

The battery 64 of the instrument 10 may comprise one or more series-connected battery cells. In various embodiments, a cell selection switch may control how many of the battery cells are being used to power the motor 65 at a given time to control the power available to the motor 65. This would allow the operator of the instrument to have greater control over both the speed and the power of the motor 65. In another embodiment, the instrument may comprise a power regulator, including, for example, a DC-to-DC converter, that regulates the voltage supplied to the motor.

Further, the voltage set point for the power regulator could be set so that the voltage delivered from the power source is less than the voltage at which the power source delivers maximum power. That way, the power source (e.g., a number of series-connected battery cells) could operate on the "left" or increasing side of the power curve, so that increases in power would be available.

In addition, according to various embodiments, the power source 64 may comprise secondary accumulator devices, such as rechargeable batteries or supercapacitors. Such secondary accumulator devices may be charged repeatedly by replaceable batteries. A charge management circuit may control the charging of the secondary accumulator devices and provide various status signals, such as an alert, when the charging of the secondary accumulator devices is complete.

In other embodiments, the power source or power pack comprising the secondary accumulator devices may be removable from the instrument and connectable to a remote charger base. The charger base may charge the secondary accumulator devices, such as from the AC electrical mains or a battery. The charger base may also comprise a processor and memory unit. Data stored in a memory of the removable power pack may be downloaded to the charger base, from which it may be uploaded for later use and analysis, such as by the user (e.g., physician), the manufacturer, or distributor of the instrument, etc. The data may comprise operating parameters, such as charge cycle information, as well as ID values for various replaceable components of the instrument, such as the staple cartridge.

More details regarding such power sources may be found in commonly assigned U.S. application Ser. No. 12/031,556, entitled "Motorized surgical cutting and fastening instrument," and Ser. No. 12/031,567, entitled "Motorized surgical cutting and fastening instrument having handle based power source,", both of which were filed on Feb. 14, 2008, and both of which are incorporated herein by reference in their entirety.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a thermoformed plastic shell covered with a sheet of TYVEK. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam and other methods.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical instrument for cutting and stapling tissue, wherein the surgical instrument comprises:
   a handle comprising:
      an electric motor; and
      a control system for controlling said electric motor, said control system comprising:
         a battery operably coupleable to said electric motor, said battery configured to supply pulses to said electric motor; and
         a pulse width modulation circuit operably coupleable to said battery, said pulse width modulation circuit configured to control the duration of pulses supplied from said battery to said electric motor;
   a shaft extending from said handle; and
   an end effector extending from said shaft, said end effector comprising:
      a replaceable staple cartridge comprising a plurality of staples for stapling tissue;
      a cutting element for cutting tissue, wherein said cutting element is configured to move at least partially through said end effector during a firing stroke to deploy said staples, wherein said electric motor is configured to drive said cutting element with an applied power during the firing stroke at a firing speed, wherein said pulse width modulation circuit is configured to reduce the speed of said cutting element to below the firing speed at various times during the firing stroke, and wherein the applied power applied to said cutting element is optimized by said pulse width modulation circuit;
      a proximal end;
      a cartridge lockout mechanism positioned in a lockout region of said end effector, wherein said pulse width modulation circuit is configured to modulate the speed of said cutting element below the firing speed as said cutting element travels within said lockout region; and
a distal end, wherein said pulse width modulation circuit is configured to modulate the speed of said cutting element below the firing speed as said cutting element approaches said distal end.

2. The surgical instrument of claim 1, wherein said cutting element is configured to move between a plurality of positions during the firing stroke, the plurality of positions comprising:
an initial range of positions;
a pre-reversing range of positions; and
a pre-stopping range of positions;
wherein said pulse width modulation circuit reduces the duration of pulses during at least one of the initial range of positions, pre-reversing range of positions, or pre-stopping range of positions.

3. The surgical instrument of claim 2, wherein said pulse width modulation circuit reduces the applied power applied to said cutting element during at least one of the initial range of positions, pre-reversing range of positions, or pre-stopping range of positions.

4. The surgical instrument of claim 1, wherein the duration of pulses varies during the firing stroke.

5. The surgical instrument of claim 1, wherein the applied power applied to said cutting element varies during the firing stroke.

6. The surgical instrument of claim 1, wherein said end effector further comprises a cutting element position sensor configured to detect a plurality of positions of said cutting element, said pulse width modulation circuit of said control system configured to control said electric motor based on the detected positions of said cutting element.

7. A surgical stapler, comprising:
a handle;
a shaft extending from said handle;
a surgical end effector extending from said shaft, wherein said surgical end effector comprises a replaceable staple cartridge;
a firing member configured to move through a plurality of positions during a firing stroke;
an electric motor configured to drive said firing member with a speed during the firing stroke;
a control system for controlling said electric motor, said control system comprising:
a battery operably engageable with said electric motor, said battery configured to supply pulses to said electric motor; and
a pulse width modulation circuit operably engageable with said battery, said pulse width modulation circuit configured to control the duration of pulses supplied from said battery to said electric motor, wherein said pulse width modulation circuit is configured to optimize the speed applied to said firing member from said electric motor;
wherein said firing member is configured to move at least partially through said surgical end effector during the firing stroke at a firing speed, wherein said pulse width modulation circuit is configured to reduce the speed of said firing member to below the firing speed at various times during the firing stroke, and wherein said surgical end effector further comprises:
a proximal end;
a cartridge lockout mechanism positioned in a lockout region, wherein said pulse width modulation circuit is configured to modulate the speed of said firing member below the firing speed as said firing member travels within said lockout region; and
a distal end, wherein said pulse width modulation circuit is configured to modulate the speed of said firing member below the firing speed as said firing member approaches said distal end.

8. The surgical stapler of claim 7, wherein the plurality of positions comprises:
an initial range of positions;
a pre-reversing range of positions; and
a pre-stopping range of positions;
wherein said pulse width modulation circuit reduces the duration of pulses during at least one of the initial range of positions, pre-reversing range of positions, or pre-stopping range of positions.

9. The surgical stapler of claim 8, wherein the said pulse width modulation circuit reduces the speed applied to said firing member during at least one of the initial range of positions, pre-reversing range of positions, or pre-stopping range of positions.

10. The surgical stapler of claim 7, wherein the duration of pulses varies during the firing stroke.

11. The surgical stapler of claim 7, wherein the speed applied to said firing member varies during the firing stroke.

12. The surgical stapler of claim 7, further comprising a firing member position sensor configured to detect a plurality of positions of said firing member, said pulse width modulation circuit of said control system configured to control said electric motor based on the detected positions of said firing member.

13. The surgical stapler of claim 7, wherein said firing member further comprises a cutting element configured to translate in said surgical end effector.

14. A surgical stapler, comprising:
a handle;
a shaft extending from said handle;
a surgical end effector extending from said shaft, wherein said surgical end effector comprises a replaceable staple cartridge;
a firing member configured to move through a plurality of positions during a firing stroke;
an electric motor configured to drive said firing member during the firing stroke;
a control system for controlling said electric motor, said control system comprising:
a battery operably engageable with said electric motor, said battery configured to supply pulses to said electric motor;
a pulse frequency modulation circuit operably engageable with said battery, said pulse frequency modulation circuit configured to control the frequency of pulses supplied from said battery to said electric motor, wherein said pulse frequency modulation circuit is configured to optimize the speed applied to said firing member from said electric motor;
wherein said firing member is configured to move at least partially through said surgical end effector during the firing stroke at a firing speed, wherein said pulse frequency modulation circuit is configured to reduce the speed of said firing member to below the firing speed at various times during the firing stroke, and wherein said surgical end effector further comprises:
a proximal end; and
a distal end, wherein said pulse frequency modulation circuit is configured to modulate the speed of said firing member below the firing speed as said firing member approaches said distal end.

15. The surgical stapler of claim 14, wherein the speed applied to said firing member varies during the firing stroke.

16. The surgical stapler of claim 14, further comprising a firing member position sensor configured to detect a plurality of positions of said firing member, said pulse frequency modulation circuit of said control system configured to control said electric motor based on the detected positions of said firing member.

17. The surgical stapler of claim 14, wherein said firing member further comprises a cutting element configured to translate in said surgical end effector.

* * * * *